United States Patent
Ahmad et al.

(10) Patent No.: US 10,487,648 B2
(45) Date of Patent: *Nov. 26, 2019

(54) ENTROPY BASED MULTIPHASE FLOW DETECTION

(71) Applicant: Saudi Arabian Oil Company, Dhahran (SA)

(72) Inventors: Talha Jamal Ahmad, Dhahran (SA); Michael John Black, Dhahran (SA); Muhammad Arsalan, Khobar (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/384,525

(22) Filed: Apr. 15, 2019

(65) Prior Publication Data

US 2019/0242252 A1    Aug. 8, 2019

Related U.S. Application Data

(63) Continuation of application No. 16/012,571, filed on Jun. 19, 2018, now Pat. No. 10,378,343, which is a
(Continued)

(51) Int. Cl.
*E21B 47/18*      (2012.01)
*G01N 29/14*     (2006.01)
(Continued)

(52) U.S. Cl.
CPC ............ *E21B 47/18* (2013.01); *E21B 47/122* (2013.01); *G01F 1/666* (2013.01); *G01F 1/74* (2013.01);
(Continued)

(58) Field of Classification Search
None
See application file for complete search history.

(56) References Cited

U.S. PATENT DOCUMENTS

| 4,667,515 A | 5/1987 | Farren et al. |
| 5,070,725 A | 12/1991 | Cox |
(Continued)

FOREIGN PATENT DOCUMENTS

| CN | 2932368 Y | 8/2007 |
| EP | 0465032 A1 | 6/1991 |
(Continued)

OTHER PUBLICATIONS

Al-Lababidi et al., "Upstream Multiphase Flow Assurance Monitoring Using Acoustic Emission", www.intechopen.com/books/acoustic-emission/multiphase-flow-assurance-monitoring-using-acoustic-emission, 2012, pp. 217-251.
(Continued)

*Primary Examiner* — Muhammad N Edun
*Assistant Examiner* — Jerold B Murphy
(74) *Attorney, Agent, or Firm* — Bracewell LLP; Constance G. Rhebergen; Ryan B. McBeth

(57) ABSTRACT

Systems, computer-implemented methods, and non-transitory computer-readable medium having a stored computer program provide characterization of multiphase fluid flow (MPF) using approximate entropy calculation techniques to enhance measuring and monitoring of a flow regime in a segment of pipe for hydrocarbon-production operations. The systems and methods can be optimized using principal component analysis.

11 Claims, 6 Drawing Sheets

Related U.S. Application Data continuation of application No. 15/189,451, filed on Jun. 22, 2016, now Pat. No. 10,030,512.

(60) Provisional application No. 62/182,786, filed on Jun. 22, 2015.

(51) Int. Cl.
| | |
|---|---|
| *G01N 29/02* | (2006.01) |
| *G01F 1/66* | (2006.01) |
| *G01F 1/74* | (2006.01) |
| *E21B 47/12* | (2012.01) |
| *G01N 29/46* | (2006.01) |

(52) U.S. Cl.
CPC .............. *G01N 29/02* (2013.01); *G01N 29/14* (2013.01); *G01N 29/46* (2013.01); *G01N 2291/02416* (2013.01); *G01N 2291/02433* (2013.01)

(56) References Cited

U.S. PATENT DOCUMENTS

| | | | |
|---|---|---|---|
| 5,146,414 A | 9/1992 | McKown | |
| 5,148,405 A | 9/1992 | Belchamber | |
| 5,207,107 A | 5/1993 | Wolf et al. | |
| 5,353,627 A * | 10/1994 | Diatschenko | G01N 29/036 73/19.03 |
| 5,415,048 A | 5/1995 | Diatschenko et al. | |
| 5,561,245 A | 10/1996 | Georgi et al. | |
| 5,619,043 A | 4/1997 | Preikschat | |
| 5,729,013 A | 3/1998 | Bergren, III | |
| 5,792,962 A | 8/1998 | Constant | |
| 6,076,049 A | 6/2000 | Lievois | |
| 6,412,352 B1 | 7/2002 | Evans et al. | |
| 6,575,043 B1 | 6/2003 | Huang et al. | |
| 6,644,119 B1 | 11/2003 | Sinha | |
| 6,672,131 B1 | 1/2004 | Aldal et al. | |
| 7,075,063 B2 | 7/2006 | Dong et al. | |
| 7,201,068 B2 | 4/2007 | Foss | |
| 7,233,001 B2 | 6/2007 | Lievois | |
| 7,274,996 B2 | 9/2007 | Lapinski et al. | |
| 7,293,471 B2 | 11/2007 | Lund Bo | |
| 7,436,514 B2 | 10/2008 | Ludwig | |
| 7,437,946 B2 * | 10/2008 | Gysling | G01F 1/66 73/861.23 |
| 7,562,584 B2 | 7/2009 | Conquergood | |
| 7,654,155 B2 | 2/2010 | Johansen | |
| 7,775,125 B2 | 8/2010 | Rhodes | |
| 8,321,133 B2 | 11/2012 | Hsu | |
| RE44,943 E | 6/2014 | O'Brien | |
| 8,916,815 B2 | 12/2014 | Xie | |
| 9,008,762 B2 | 4/2015 | Brockway | |
| 9,689,802 B2 | 6/2017 | Caseres et al. | |
| 10,030,511 B2 | 7/2018 | Ahmad et al. | |
| 10,030,512 B2 * | 7/2018 | Ahmad | E21B 47/122 |
| 2002/0029883 A1 | 3/2002 | Vinegar et al. | |
| 2007/0068242 A1 | 3/2007 | DiFoggio | |
| 2007/0288178 A1 | 12/2007 | Bonnefous | |
| 2008/0163692 A1 * | 7/2008 | Huang | G01F 1/663 73/627 |
| 2009/0152475 A1 | 6/2009 | Sasaki et al. | |
| 2010/0145634 A1 | 6/2010 | Pinguet | |
| 2011/0036177 A1 | 2/2011 | Pinguet et al. | |
| 2012/0046870 A1 | 2/2012 | Lievois et al. | |
| 2012/0323502 A1 | 12/2012 | Tanoura | |
| 2013/0016336 A1 | 1/2013 | Xie | |
| 2014/0076547 A1 | 3/2014 | Unalmis | |
| 2014/0110105 A1 | 4/2014 | Jones | |
| 2014/0260659 A1 | 9/2014 | Sheila-Vadde | |
| 2015/0377667 A1 * | 12/2015 | Ahmad | G01N 29/14 702/48 |

FOREIGN PATENT DOCUMENTS

| | | |
|---|---|---|
| EP | 2199755 A1 | 6/2010 |
| GB | 2426579 A | 11/2006 |
| WO | 9823931 A1 | 6/1998 |
| WO | 0045133 A1 | 8/2000 |
| WO | 2004063741 A2 | 7/2004 |

OTHER PUBLICATIONS

Arridge, S R et al. "The use of multiple data types in time-resolved optical absorption and scattering tomography (TOAST)," Proc. SPIE 2035 p. 218-229. (1993).

Carvalho, "Application of the unltrasonic technique and high-speed filiming for the study of the structure of air-water bubbly flows", Experimental Thermal and Fluid Science, Elsevier Science Inc., New York, US, vol. 33, No. 7, Oct. 1, 2009, pp. 1065-1086.

International Search Report and Written Opinion for related PCT application PCT/US2016/038641 dated Sep. 21, 2016.

International Search Report and Written Opinion for related PCT application PCT/US2016/038660 dated Sep. 21, 2016.

International Search Report and Written Opinion for related PCT application PCT/US2016/040980 dated Oct. 24, 2016.

Gao et al., "Flow-pattern identification and nonlinear dynamics of gas-liquid two-phase flow in complex networks", Physical Review, 2009, pp. 1-14, vol. 79, The American Physical Society.

Kam OWD Water Cut Meter—by Kam Controls Inc., http://www.kam.com/kam-products/owd-oil-water-detector/ accessed Sep. 14, 2016 (2 pages).

Norgaard et al., "Principal Component Analysis and Near Infrared Spectroscopy", A white paper from FOSS, pp. 1-7.

PhaseDynamics; CCM Multiphase Meters; http://www.phasedynamics.com accessed Sep. 14, 2016 (pp. 1-5).

Pincus, "Approximate entropy as a measure of system complexity", Mathematics, 1991, pp. 2297-2301, vol. 88, Proceedings of the National Academy of Sciences.

Roxar Watercut meter (WCM) by Emerson Process Management http://www2.emersonprocess.com/en-us/brands/roxar/flowmetering/meteringsystems/pages/roxarwatercutmeter.aspx accessed Sep. 14, 2016 (1 page).

Schlumberger "Vx Multiphase Well Testing Technology" http://www.slb.com/services/characterization/testing/multiphase/vx_technology.aspx accessed Sep. 14, 2016 (1 page).

Weatherford International "Flow Measurement" http://www.weatherford.com/en/products-services/production/flow-measurement accessed Sep. 14, 2016 (pp. 1-6).

Zelentech; Watercut monitor by Zelentech, http://www.zelentech.co/products/watercut.php accessed Sep. 14, 2016 (pp. 1-4).

Zhangshuan, H. Reservoir-parameter identification using minimum relative entrophy-based Bayesian inversion of seismic AVA and marine CSEM data, Geophysics, vol. 71, No. 6, (Nov.-Dec. 2006); pp. 077-088.

* cited by examiner

ENTROPY BASED MULTIPHASE FLOW DETECTION

PRIORITY

This application is a continuation of and claims priority to U.S. patent application Ser. No. 16/012,571, filed Jun. 19, 2018. U.S. patent application Ser. No. 16/012,571 is a continuation of U.S. patent application Ser. No. 15/189,451, filed Jun. 22, 2016, which claims priority to and the benefit of U.S. Prov. App. Ser. No. 62/182,786, filed Jun. 22, 2015, the entire disclosure of which is incorporated here by reference.

BACKGROUND

Embodiments of the disclosure relate to systems and methods for characterizing multiphase fluid flow (MPF) in a pipe.

The simultaneous flow of two or more physical phases is referred to as multiphase fluid flow (MPF). The flow behavior of MPF is more complex than for single phase flow regime patterns. The flow regime in MPF can depend on a number of factors including, for example, the relative density ratio of one fluid to another, difference in viscosity between different fluids, and the velocity (slip) of each fluid. MPF can include any combination of two or more phases including solid, liquid, and gas. For example, one MPF might include sand, oil, and natural gas. Accurate measurement and characterization of MPF regimes is important to optimize production from hydrocarbon-producing wells and to determine the composition and amount of production streams.

Systems and methods have been proposed for non-intrusive measurement of MPF parameters including, for example, flow regime, flow rate, presence of solid content, and volume and mass ratios of individual phases relative to one another. Active systems include those that convey any one of or any combination of acoustic and ultrasound frequencies through the flow and analyze the received acoustic responses.

Non-invasive systems and methods that utilize acoustic emissions and signals to identify various flow regimes and the presence of solid content in MPF employ a variety of parameters from flow acoustic data such as, for example, signal amplitude, root-mean-square (RMS) value, energy, and basic frequency content. Such systems and methods typically apply thresholding and template matching techniques. One of the many challenges posed by existing systems and methods includes the presence of continuous and random background acoustic and electric noise in MPF systems.

SUMMARY OF THE INVENTION

Applicant has recognized that there is a need for accurate and efficient measurement systems and methods for characterizing multiphase fluid flow (MPF). Applicant also has recognized that using approximate entropy calculations and techniques with the systems and methods of the present disclosure allows for accurate, real-time measurement and characterization of MPF. Embodiments of the present disclosure are non-radioactive, do not impede flow in any way, and are computationally efficient. Embodiments of the present disclosure will allow non-intrusive measurement of various MPF parameters in any one of or any combination of a pipe, pipeline, casing, liner, and tubing, and will identify the presence of solids, such as, for example, sand, in the MPF. Certain embodiments will enable non-intrusive, low-cost, small, accurate meters for measurement and characterization of MPF regimes and MPF characteristics, which will improve monitoring, production, and reservoir management in hydrocarbon-retrieval applications.

Moreover, Applicant has recognized a statistical-based approach that can quantify short-term and long-term complexity and randomness in MPF using approximate entropy calculations. Different MPF flow regimes will exhibit different values of statistical randomness, especially over shorter time periods. Principal component analysis is used to optimize certain embodiments of the present disclosure.

Having recognized deficiencies in existing systems and methods for measuring MPF, the sources of these deficiencies, and solutions to the deficiencies, Applicant discloses embodiments of systems, computer-implemented methods, and a non-transitory, computer-readable medium having stored computer programs to provide passive and active systems and methods for characterizing MPF and thereby enhance measuring and monitoring of a flow regime in a segment of pipe for hydrocarbon-production operations. Hydrocarbon-production operations can refer to any upstream or downstream production concerning hydrocarbons in any form, including, but not limited to, crude oil, natural gas, natural gas condensates, liquefied petroleum gas, heavy products, light products, and distillates.

Embodiments of the disclosure can include a passive multiphase fluid flow (MPF) characterization system to enhance measuring and monitoring of a flow regime in a segment of pipe for hydrocarbon-production operations. The system includes an acoustic emission sensor disposed proximate to the segment of pipe and operable to receive an acoustic emission from a MPF, the segment of pipe operable to support the MPF in hydrocarbon-production operations including at least two physical phases, and the acoustic emission sensor operable to convert the received acoustic emission to an electrical signal. The system further includes a processing unit, including a processor, operable to receive the electrical signal and transform the electrical signal to characterize the MPF, the processing unit in communication with and comprising non-transitory, tangible memory medium in communication with the processor having a set of stored instructions, the set of stored instructions being executable by the processor. The processor executes the steps of segmenting the electrical signal into short term, medium term, and long term time series, and assigning positive real numbers to the time series, the positive real numbers including larger values and smaller values, the larger values corresponding to process randomness, and the smaller values corresponding to instances of recognizable patterns in the electrical signal.

The processor further executes the steps of categorizing certain positive real numbers as outlier values, calculating short term, medium term, and long term approximate entropy values for the MPF responsive to the short term, medium term, and long term time series from the electrical signal, and comparing the short term, medium term, and long term approximate entropy values for the MPF to pre-determined short term, medium term, and long term approximate entropy values. The processor further executes the step of determining characteristics of the MPF responsive to similarities between the short term, medium term, and long term approximate entropy values for the MPF and the pre-determined short term, medium term, and long term approximate entropy values. The processing unit further includes a user interface coupled to the processing unit, the user interface operable to accept user inputs to control the processing unit, and operable to display the characteristics of the MPF to a user.

In some embodiments, the system further comprises a database with pre-determined short term, medium term, and long term approximate entropy values for a variety of MPF flow regimes. In other embodiments, the system further comprises a preamplifier coupled to the acoustic emission sensor, and operable to receive and amplify the electrical signal from the acoustic emission sensor. In some embodiments, the system further comprises a band-pass signal filter coupled to the preamplifier, the band-pass signal filter operable to receive an amplified electrical signal from the preamplifier, and further operable to remove acoustic background noise from useful MPF acoustic information contained within the amplified electrical signal, responsive to programmed cutoff frequencies in the band-pass signal filter derived from an operating frequency and bandwidth of the acoustic emission sensor.

Still in other embodiments, the system includes an analog-to-digital converter coupled to the band-pass signal filter, the analog-to-digital converter operable to receive from the band-pass signal filter the useful MPF acoustic information, and operable to convert the useful MPF acoustic information to a digital signal. In some embodiments of the system, the acoustic emission sensor comprises a first acoustic emission sensor, and the system further comprises a second acoustic emission sensor disposed proximate to the segment of pipe and operable to receive an acoustic emission from the MPF, the second acoustic emission sensor further operable to convert the received acoustic emission to an electrical signal.

In some embodiments of the system, the second acoustic emission sensor is disposed at a distance D from the first acoustic emission sensor, where the distance D is operable to allow coherent measurements of the MPF in a substantially similar state at both the first acoustic emission sensor and the second acoustic emission sensor, and where an accurate measurement of flow velocity of the MPF is obtained by dividing the distance D by a difference in time between a first time at which the MPF passes the first acoustic emission sensor and a second time at which the MPF passes the second acoustic emission sensor.

Still in other embodiments of the system, the processing unit further is operable to execute a set of instructions to conduct a principal component analysis on the system including the steps of gathering acoustic emission data under a variety of flow parameters in situations in which an appropriate Reynolds number is known for the MPF for which data is being gathered forming time series of acoustic waveforms, and performing a Fourier Transformation on the data, the data being converted into measurements of acoustic power as a function of frequency. The principal component analysis further comprises the steps of executing a suite of measurements using a test matrix including different conditions of the MPF including at least one variable selected from the group consisting of stepped values of watercut, stepped values of total liquid flow, and MPF regimes, and post-processing the data by applying principal component analysis to the data to determine measurable frequencies relevant to determining the characteristics of the MPF.

Some embodiments of the system further comprise an optimized acoustic emission sensor, where the optimized acoustic emission sensor is operable to receive the frequencies determined by the principal component analysis to be relevant to determining the characteristics of the MPF.

Further disclosed is an active multiphase fluid flow (MPF) characterization system to enhance measuring and monitoring of a flow regime in a segment of pipe for hydrocarbon-production operations. The system includes an acoustic receiver disposed proximate to the segment of pipe and operable to receive an acoustic signal transmitted through a MPF, the segment of pipe operable to support the MPF in hydrocarbon-production operations including at least two physical phases, and the acoustic receiver operable to convert the received acoustic signal to an electrical signal. The system further includes an acoustic transmitter disposed proximate to the segment of pipe and operable to convey an acoustic signal through the MPF in hydrocarbon-production operations, further operable to convey the acoustic signal such that the acoustic signal is receivable by the acoustic receiver. The system further includes a processing unit, including a processor, operable to receive the electrical signal and transform the electrical signal to characterize the MPF.

The processing unit is in communication with and includes non-transitory, tangible memory medium in communication with the processor having a set of stored instructions, the set of stored instructions being executable by the processor and including the steps of segmenting the electrical signal into short term, medium term, and long term time series and assigning positive real numbers to the time series, the positive real numbers including larger values and smaller values, the larger values corresponding to process randomness, and the smaller values corresponding to instances of recognizable patterns in the electrical signal. The set of instructions further includes the steps of categorizing certain positive real numbers as outlier values and calculating short term, medium term, and long term approximate entropy values for the MPF based upon the short term, medium term, and long term time series from the electrical signal. The set of instructions further includes the steps of comparing the short term, medium term, and long term approximate entropy values for the MPF to pre-determined short term, medium term, and long term approximate entropy values and determining characteristics of the MPF responsive to similarities between the short term, medium term, and long term approximate entropy values for the MPF and the pre-determined short term, medium term, and long term approximate entropy values.

The processing unit further includes a user interface coupled to the processing unit, the user interface operable to accept user inputs to control the processing unit, and operable to display the characteristics of the MPF to a user. In some embodiments, the active system further includes a database with pre-determined short term, medium term, and long term approximate entropy values for a variety of MPF flow regimes. In some embodiments, the system further includes a preamplifier coupled to the acoustic receiver, and operable to receive and amplify the electrical signal from the acoustic receiver. In other embodiments, the system further includes a band-pass signal filter coupled to the preamplifier, the band-pass signal filter operable to receive an amplified electrical signal from the preamplifier, and further operable to remove acoustic background noise from useful MPF acoustic information contained within the amplified electrical signal, responsive to programmed cutoff frequencies in the band-pass signal filter derived from an operating frequency and bandwidth of the acoustic receiver.

In some embodiments, the system further includes an analog-to-digital converter coupled to the band-pass signal filter, the analog-to-digital converter operable to receive from the band-pass signal filter the useful MPF acoustic information, and operable to convert the useful MPF acoustic information to a digital signal. In other embodiments, the system further includes an amplifier disposed proximate the acoustic transmitter and operable to receive and amplify a drive signal to provide an amplified signal to the acoustic transmitter, where the amplifier is a high-voltage amplifier operable from about 50 volts (V) to about 100 V.

In some embodiments of the system, the acoustic receiver comprises a first acoustic receiver, and the system further comprises a second acoustic receiver disposed proximate to the segment of pipe and operable to receive an acoustic signal transmitted through the MPF, the second acoustic receiver further operable to convert the received acoustic signal to an electrical signal, and a second acoustic transmitter disposed proximate to the segment of pipe and operable to convey an acoustic signal through the MPF in hydrocarbon-production operations, further operable to convey the acoustic signal such that the acoustic signal is receivable by the second acoustic receiver.

In some embodiments of the system, the second acoustic receiver is disposed at a distance D from the first acoustic receiver, where the distance D is operable to allow coherent measurements of the MPF in a substantially similar state at both the first acoustic receiver and the second acoustic receiver, and where an accurate measurement of flow velocity of the MPF is obtained by dividing the distance D by a difference in time between a first time at which the MPF passes the first acoustic receiver and a second time at which the MPF passes the second acoustic receiver.

In other embodiments of the active system, the processing unit further is operable to execute a set of instructions to conduct a principal component analysis on the system including the steps of gathering acoustic signal data under a variety of flow parameters in situations in which an appropriate Reynolds number is known for the MPF for which data is being gathered, forming time series of acoustic waveforms, performing a Fourier Transformation on the data, the data being converted into measurements of acoustic power as a function of frequency, executing a suite of measurements using a test matrix including different conditions of the MPF including at least one variable selected from the group consisting of stepped values of watercut, stepped values of total liquid flow, and MPF regimes, and post-processing the data by applying principal component analysis to the data to determine measurable frequencies relevant to determining the characteristics of the MPF.

In some embodiments of the system, the system further includes an optimized acoustic receiver, where the optimized acoustic receiver is operable to receive the frequencies determined by the principal component analysis to be relevant to determining the characteristics of the MPF.

Additionally disclosed is a method for characterizing multiphase fluid flow (MPF) to enhance measuring and monitoring of a flow regime in a segment of pipe for hydrocarbon-production operations. The method comprises the steps of sensing an acoustic emission from a MPF, the segment of pipe operable to support the MPF in hydrocarbon-production operations including at least two physical phases and converting the acoustic emission to an electrical signal. The method further includes the steps of segmenting the electrical signal into short term, medium term, and long term time series, and assigning positive real numbers to the time series, the positive real numbers including larger values and smaller values, the larger values corresponding to process randomness, and the smaller values corresponding to instances of recognizable patterns in the electrical signal. The method further includes the steps of categorizing certain positive real numbers as outlier values, and calculating short term, medium term, and long term approximate entropy values for the MPF responsive to the short term, medium term, and long term time series from the electrical signal.

The method further includes the steps of comparing the short term, medium term, and long term approximate entropy values for the MPF to pre-determined short term, medium term, and long term approximate entropy values and determining characteristics of the MPF responsive to similarities between the short term, medium term, and long term approximate entropy values for the MPF and the pre-determined short term, medium term, and long term approximate entropy values.

In some embodiments, the method further comprises the step of displaying the characteristics of the MPF on a user interface, where the user interface is operable to graphically represent at least one flow regime. In some embodiments, the method further comprises the step of preamplifying the electrical signal before the step of segmenting the electrical signal. In other embodiments, the method includes the step of filtering the electrical signal, before segmenting the electrical signal, responsive to programmed cutoff frequencies in a band-pass signal filter derived from an operating frequency and bandwidth of an acoustic emission sensor. Still in other embodiments, the method further comprises the step of converting the electrical signal to a digital signal, before segmenting the electrical signal.

In some embodiments of the method, the step of sensing an acoustic emission comprises the step of sensing a first acoustic emission, and further comprises the step of sensing a second acoustic emission from the MPF, the second acoustic emission being sensed simultaneously with and at a distance D from the first acoustic emission. In other embodiments of the method, the method includes the step of calculating an accurate measurement of flow velocity of the MPF in response to the distance D and sensing the first acoustic emission and sensing the second acoustic emission. Still in other embodiments, the method includes the step of conducting a principal component analysis, where the principal component analysis comprises the steps of gathering acoustic emission data under a variety of flow parameters in situations in which an appropriate Reynolds number is known for the MPF for which data is being gathered and forming time series of acoustic waveforms.

The principal component analysis further comprises the steps of performing a Fourier Transformation on the data, the data being converted into measurements of acoustic power as a function of frequency, executing a suite of measurements using a test matrix including different conditions of the MPF including at least one variable selected from the group consisting of stepped values of watercut, stepped values of total liquid flow, and multiphase flow patterns, and post-processing the data by applying principal component analysis to the data to determine measurable frequencies relevant to determining the characteristics of the MPF. In some embodiments, the method further comprises the step of optimizing the step of sensing an acoustic emission from the MPF to receive the frequencies determined by the principal component analysis to be relevant to determining the characteristics of the MPF.

Additionally disclosed is a method for characterizing multiphase fluid flow (MPF) to enhance measuring and monitoring of a flow regime in a segment of pipe for hydrocarbon-production operations. The method comprises the steps of transmitting an acoustic signal through a MPF, receiving an acoustic signal transmitted through the MPF, the segment of pipe operable to support the MPF in hydrocarbon-production operations including at least two physical phases, and converting the acoustic signal to an electrical signal. The method further comprises the steps of segmenting the electrical signal into short term, medium term, and long term time series, assigning positive real numbers to the time series, the positive real numbers including larger values and smaller values, the larger values corresponding to process randomness, and the smaller values corresponding to instances of recognizable patterns in the electrical signal, and categorizing certain positive real numbers as outlier values.

The method further includes the steps of calculating short term, medium term, and long term approximate entropy values for the MPF responsive to the short term, medium term, and long term time series from the electrical signal, comparing the short term, medium term, and long term approximate entropy values for the MPF to pre-determined short term, medium term, and long term approximate entropy values, and determining characteristics of the MPF responsive to similarities between the short term, medium term, and long term approximate entropy values for the MPF and the pre-determined short term, medium term, and long term approximate entropy values.

In some embodiments, the method further comprises the step of displaying the characteristics of the MPF on a user interface, where the user interface is operable to graphically represent at least one flow regime. In other embodiments, the method further comprises the step of preamplifying the electrical signal before the step of segmenting the electrical signal. Still in other embodiments, the method further comprises the step of filtering the electrical signal, before segmenting the electrical signal, responsive to programmed cutoff frequencies in a band-pass signal filter derived from an operating frequency and bandwidth of an acoustic receiver. In some embodiments, the method further comprises the step of converting the electrical signal to a digital signal, before segmenting the electrical signal.

In some embodiments of the method, the step of receiving an acoustic signal comprises the step of receiving a first acoustic signal, and further comprises the step of receiving a second acoustic signal transmitted through the MPF, the second acoustic signal being received simultaneously with and at a distance D from the first acoustic signal, and where the step of transmitting an acoustic signal comprises the step of transmitting a first acoustic signal, and further comprises the step of transmitting a second acoustic signal through the MPF, the second acoustic signal being conveyed simultaneously with and at a distance D from the first acoustic signal.

Still in other embodiments of the method, included are the steps of calculating an accurate measurement of flow velocity of the MPF in response to the distance D and receiving the first acoustic signal and receiving the second acoustic signal. Some embodiments include the step of performing a principal component analysis, where the principal component analysis comprises the steps of gathering acoustic signal data under a variety of flow parameters in situations in which an appropriate Reynolds number is known for the MPF for which data is being gathered and forming time series of acoustic waveforms. The principal component analysis further includes the steps of performing a Fourier Transformation on the data, the data being converted into measurements of acoustic power as a function of frequency, executing a suite of measurements using a test matrix including different conditions of the MPF including at least one variable selected from the group consisting of stepped values of watercut, stepped values of total liquid flow, and multiphase flow patterns, and post-processing the data by applying principal component analysis to the data to determine measurable frequencies relevant to determining the characteristics of the MPF.

In some embodiments, the method further includes the step of optimizing the step of receiving an acoustic signal from the MPF to receive the frequencies determined by the principal component analysis to be relevant to determining the characteristics of the MPF.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION OF THE INVENTION

So that the manner in which the features and advantages of the embodiments of methods, systems, and a non-transitory, computer-readable medium having stored computer programs, as well as others, which will become apparent, may be understood in more detail, a more particular description of the embodiments of methods, systems, and non-transitory, computer-readable medium having stored computer programs of the present disclosure briefly summarized previously may be had by reference to the embodiments thereof, which are illustrated in the appended drawings, which form a part of this specification. It is to be noted, however, that the drawings illustrate only various embodiments of the disclosure of methods, systems, and non-transitory, computer-readable medium having stored computer programs of the present disclosure and are therefore not to be considered limiting of the embodiments of methods, systems, and non-transitory, computer-readable medium having stored computer programs of the present disclosure's scope, as it may include other effective embodiments as well.

Figure 1:
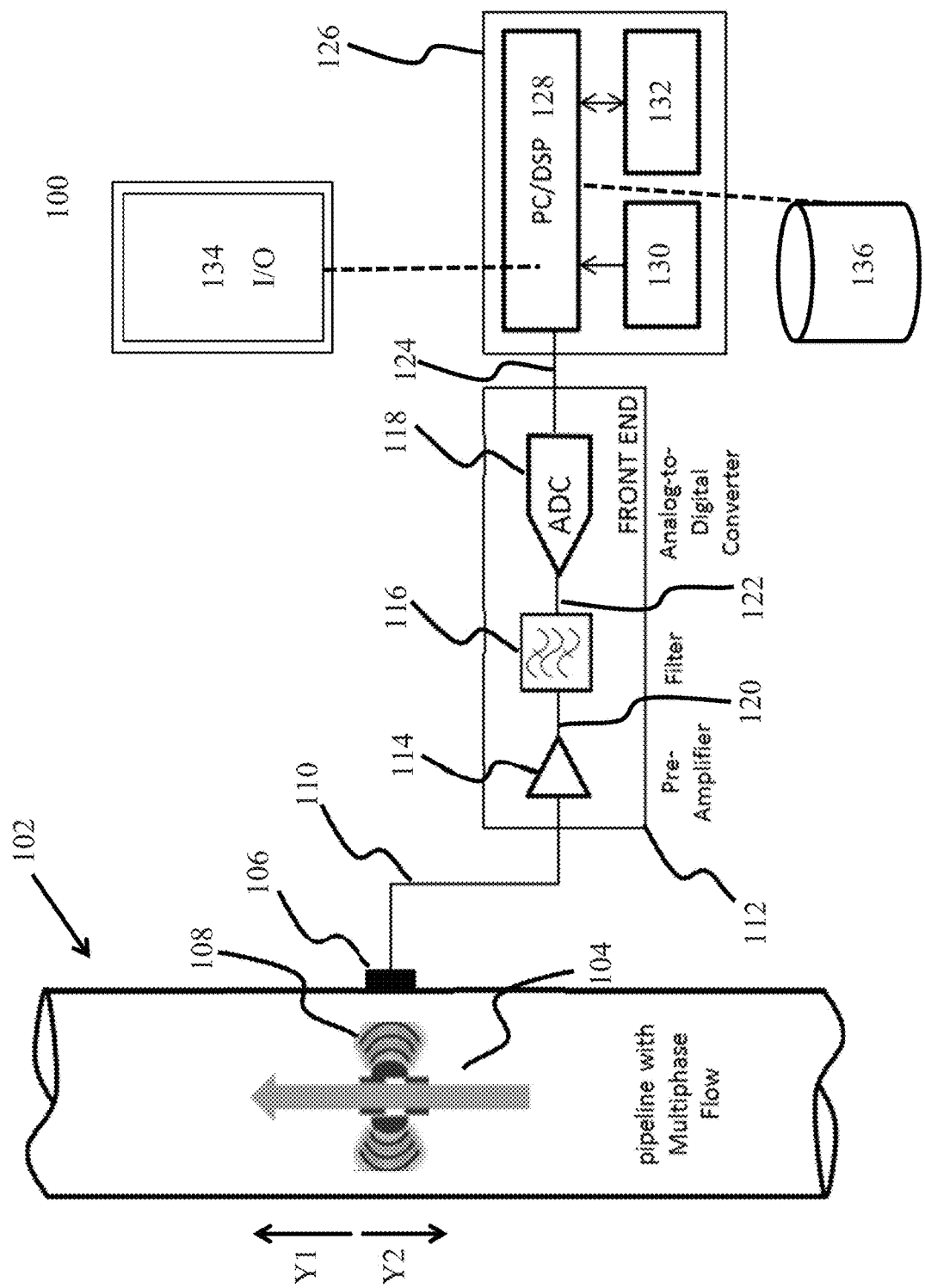
FIG. 1 is a schematic diagram of a passive system according to an embodiment of the present disclosure.

Referring now to FIG. 1, a schematic diagram of a passive acoustic emissions based system 100, according to one embodiment of the present disclosure, is shown. In the embodiment of FIG. 1, the passive acoustic emissions based system 100 includes a pipeline 102 with at least one segment 104 operable to support multiphase fluid flow (MPF). While FIG. 1 shows MPF directed in the Y1 direction, system 100 is capable of supporting MPF in either the Y1 or Y2 direction. Acoustic emission in MPF is defined as a physical phenomenon which occurs within and on the surface of the MPF, and results in spontaneous release of acoustic energy in a broad frequency range of about 1 kilohertz (kHz) to about 1 megahertz (MHz).

In some embodiments, the Y1 direction is the uphole direction in a well environment or is the upstream direction in a pipeline environment. In some embodiments, the Y2 direction is the downhole direction in a well environment or is the downstream direction in a pipeline environment. One of ordinary skill in the art would understand that MPF can have counter-flows and turbulence, but the flow is generally going towards or away from the surface in a well environment and towards or away from a pressure generating source, such as a pump, in a pipeline environment.

Systems and methods of the present disclosure are compatible for use with any pipe or pipeline capable of supporting MPF, including, but not limited to, above-ground pipelines, below-surface pipelines, under-water pipelines, pipelines within a wellbore, and pipelines used indoors, for example in a lab setting or pilot plant. "Pipes" and "pipelines" within a wellbore may include any one of or any combination of conduits, enclosed flow channels, coiled tubing, a drill pipe, a production line, completion casing, and drill casing.

Challenges confronting existing systems in pipelines include very low signal-to-noise (SNR) ratios and the stochastic nature of acoustic emission signals. Moreover, other deficiencies include intrusiveness of commercially-available metering systems, high power consumption, use of radioactive sources, high cost, high complexity, and large physical size. Because of these and other deficiencies in existing systems and methods, most are unable to provide accurate measurements and characterizations of MPF in practical industrial scenarios. For example, one such environment is a downhole environment in which many interrelated factors affect the acoustics of MPF in a complex manner. Also, existing systems and methods do not account for acoustic variabilities and the non-stationary nature of the acoustic emission (AE) signal.

Certain characteristics of MPF are described in "Upstream Multiphase Flow Assurance Monitoring Using Acoustic Emission," 2012 by Al-Lababidi, S.; Mba, D.; and Addali, A. Cranfield University, UK. Acoustic emission from MPF is dependent upon, in part, gas bubble formation and cavitation, regime breakage and coalescence, and interaction of various phases within MPF. These characteristics vary for different MPF regimes, flow rates, and also for different relative amounts of liquid, gas/vapor, and solids in the MPF. In general, acoustic information is used in the embodiments of the present disclosure to characterize the MPF as well as to determine flow characteristics. For example, the proposed systems and methods can be used to identify the MPF regime (such as a slug flow), and can be used to identify individual characteristics of the MPF (such as slug flow frequency).

Still referring to FIG. 1, the system 100 includes an acoustic emission sensor 106 mounted to the segment 104 of the pipeline 102. In the system 100, the acoustic emission sensor 106 is a passive device used to receive wideband acoustic emissions (usually in a range of several kHz) from the MPF. Acoustic emission sensor 106 performs one or more of receiving, storing, processing, and conveying MPF acoustic emissions 108. The acoustic emission sensor 106 is operable to receive acoustic emissions with frequencies up to about 1 MHz in order to detect useful MPF acoustic emissions from the flow, such as the MPF acoustic emissions 108. The acoustic emission sensor includes a microphone in some embodiments, and includes a commercially available acoustic emission sensor/transducer in some embodiments.

For example, the AE1045S from Vallen Systems, headquartered in Icking Germany, with a frequency range of about 100 kHz to about 1500 kHz, can be used. Simultaneously or alternatively a general purpose wideband acoustic emission sensor can be used, such as those commercially available from Mistras Group Ltd., headquartered in Princeton Junction, N.J. One such general purpose wideband acoustic emission sensor, for example, is the model WSA general purpose wideband sensor, with an operating frequency range of between about 100 kHz and about 1000 kHz.

Figure 2:
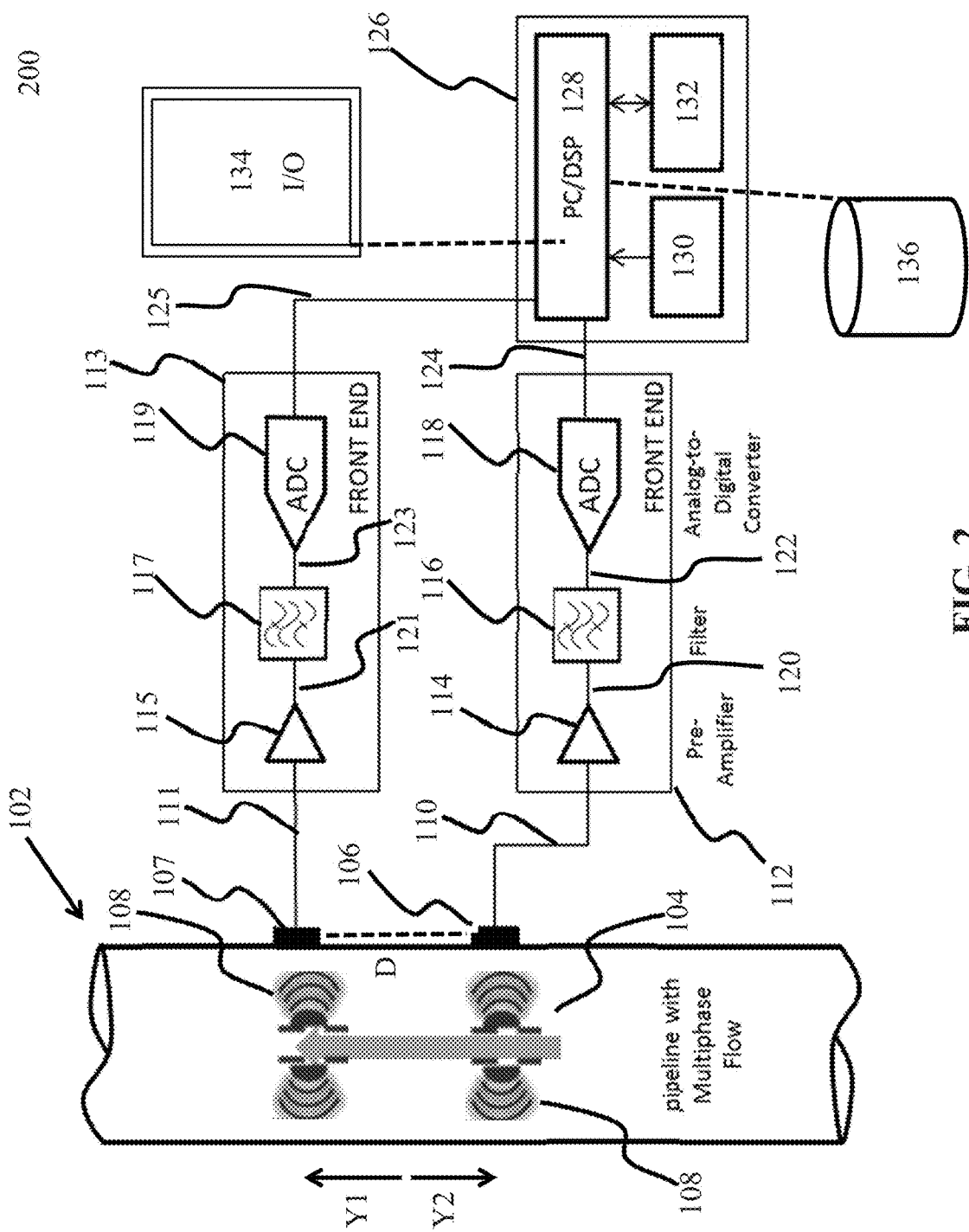
FIG. 2 is a schematic diagram of a passive system according to an embodiment of the present disclosure.

In the embodiments of passive systems of the present disclosure, such as FIGS. 1 and 2, acoustic emission sensors, such as acoustic emission sensor 106, are mounted exterior to a pipe or mounted within a hole bored in the pipe, such that the surface of the acoustic emission sensor is in contact with the MPF. In some embodiments, a preferable configuration is to have the acoustic emission sensor mounted exterior to the pipe, as the presence of the sensor interior to the pipe may impede or otherwise negatively impact the flow. In some instances, if an acoustic emission sensor is placed in the flow path, the interaction of the MPF with the sensor will generate additional undesirable acoustic emissions that are not representative of the MPF.

The frequency or frequencies received by an acoustic emission sensor will not be negatively impacted if the emission sensor is mounted exterior to the pipe. Alternatively, an acoustic emission sensor can be advantageously mounted in a hole bored in the pipe if the MPF is not impeded. Acoustic emission parameters that are affected by the location of the acoustic emission sensor include the signal amplitude and the signal-to-noise (SNR) ratio. If the sensor is mounted in a hole bored in the pipe, the received acoustic emissions will have greater amplitude and a better SNR.

If the sensor is mounted on the exterior of the pipe, the amplitude of the received acoustic emission will be weaker (as the emission will have to travel through the pipe wall). Also, with the acoustic emission sensor mounted exteriorly to the pipe wall, additional noise may travel through the pipe wall to the sensor that is not relevant to determining MPF characteristics. However, as noted previously, mounting acoustic emission sensors exterior to the pipe creates a non-invasive system. An acoustic emission sensor can be clamped or coupled to a segment of pipe by any suitable means known in the art, such as for example any one of or any combination of clamps, adhesives, bolts, screws, and straps.

More than one acoustic emission sensor can be used in the systems and methods of the present disclosure, for example as shown in FIG. 2. In some embodiments, a couplant is required to couple an acoustic emission sensor in a suitable position with a pipeline. In the system of FIG. 1, glycerol or oil based couplant is used to properly dispose the acoustic emission sensor 106 on the exterior of segment 104 to receive the MPF acoustic emissions 108. Once the acoustic emission sensor 106 receives the MPF acoustic emissions 108, the acoustic emission sensor 106 converts the MPF acoustic emissions 108 to electrical signals. These electrical signals are analog electrical signals, suited for later conversion to digital signals, in the embodiment of FIG. 1. In other embodiments, these electrical signals can be conveyed from the acoustic emission sensor as a digital signal directly to a processing unit.

In some embodiments, when an acoustic emission sensor is mounted exterior to a pipe wall, a couplant is required to remove any air from the interface between the pipe wall and the sensor. Air can be introduced due to the microstructure and surface roughness of the two contacting surfaces of the interface between the acoustic emission sensor and the pipe wall. One reason to avoid having air between an acoustic emission sensor and a pipe wall is that the acoustic impedance of air is lesser (almost 5 orders of magnitude) than a pipe surface or a sensor face. This low acoustic impedance allows for very little transmission of acoustic energy from the pipe wall to the sensor without a couplant, because most of the acoustic energy is lost. The use of a couplant can greatly improve the transmission of an acoustic emission from a MPF, through the pipe wall, and to the acoustic emission sensor. A thin layer of couplant is placed between the pipe wall surface and the sensor face. Couplants with high acoustic impedance can provide better acoustic energy transmissions and better SNR. Examples of such couplants include glycerol and propylene glycol.

As shown in FIG. 1, the acoustic emission sensor 106 is coupled by a connection 110 to a signal conversion unit 112. The connection 110 can be a wired or wireless connection, and the MPF acoustic emissions 108 received and converted to electrical signals by the acoustic emission sensor 106 are conveyed to the signal conversion unit 112. Electrical signals arising from the MPF acoustic emissions 108 are transferred from the acoustic emission sensor 106 to the signal conversion unit 112 via any one of or any combination of a cloud-based storage medium, wired connection, and wireless connection.

In the embodiment of FIG. 1, the signal conversion unit 112 includes a preamplifier 114, a band-pass signal filter 116, and an analog-to-digital converter 118. In other embodiments, the signal conversion unit includes more or fewer signal conversion units. In other embodiments, the preamplifier, the band-pass signal filter, and the analog-to-digital converter are not part of a single unit, such as the signal conversion unit 112. The signal conversion unit, in some embodiments, includes hardware and a non-transitory, tangible memory medium in communication with a processor having a stored set of instructions.

The MPF acoustic emissions 108 detected by the acoustic emission sensor 106 are a combination of useful MPF acoustic information, which is used to characterize the flow regime of the MPF, and random acoustic background noise from the environment surrounding the pipeline 102. The converted electrical signal produced by the acoustic emission sensor 106 and transferred to the preamplifier 114 by the connection 110 is amplified by the preamplifier 114 to produce an amplified electrical analog signal. In some embodiments, more than one preamplifier is used. The amplified electrical analog signal is then conveyed by a connection 120 to the band-pass signal filter 116.

Similar to the connection 110, the connection 120 can be a wired or wireless connection, and the amplified electrical signal is conveyed to the band-pass signal filter 116. The amplified electrical signal can be transferred from the preamplifier to the band-pass signal filter via any one of or any combination of a cloud-based storage medium, wired connection, and wireless connection.

After the electrical analog signal is amplified by the preamplifier 114, the signal is filtered using the band-pass signal filter 116. The cutoff frequencies of the band-pass signal filter 116 depend, in the embodiment of FIG. 1, on the operating frequency and bandwidth of the acoustic emission sensor 106. In other embodiments, the cutoff frequencies of the band-pass signal filter can be adjusted by user inputs or adjusted according to MPF flow conditions, composition of the MPF, or other environmental conditions. The band-pass signal filter 116 filters out or removes certain undesirable frequencies that are not useful for characterizing the MPF regime, such as noise caused by the environment surrounding the pipeline 102.

In some embodiments, the band-pass signal filter can be used to remove any unwanted noise signal and improve the SNR. For example, in active system configurations, such as those shown in FIGS. 3 and 4 and described as follows, when an acoustic signal of fixed frequency is transmitted through the MPF, a band-pass filter is used to limit the received signal to the known transmitted frequency or frequencies and remove all other frequencies from the signal. Also for passive configurations of the system, such as those of FIGS. 1 and 2, the required frequencies of interest for acoustic emissions from the MPF might be in a certain frequency range for a certain application, and remaining, irrelevant frequencies are removed. These frequency ranges are determined in the lab by experimentation. Also for passive configurations, such as FIGS. 1 and 2, acoustic emission frequencies less than about 20 kHz are usually removed.

In some embodiments, an off-the-shelf integrated circuit (IC) with specific programming can be used to implement a band-pass filter, such as band-pass signal filter 116. Many such IC's are available commercially, for example from Texas Instruments, headquartered in Dallas, Tex., or Analog Devices, headquartered in Norwood, Mass. Commercial front-end solutions are also available for the signal conversion units, such as signal conversion units 112, 113, and the band-pass signal filters 116, 117. The Active AFE5803 fully-integrated, 8-channel ultrasound analog front end from Texas Instruments is one such commercial front end solution. Such devices can be programmed through serial interface by sending specific device commands from a personal computing device, such as a personal computer or mobile device. Also, a custom application specific integrated circuit (ASIC) can be developed for any one of or any combination of signal conversion units 112, 113 and band-pass signal filters 116, 117.

After the amplified electrical analog signal is filtered by the band-pass signal filter 116, a filtered electrical analog signal is transferred from the band-pass signal filter 116 to the analog-to-digital converter 118 (ADC) by a connection 122. Similar to the connection 110 and the connection 120, the connection 122 can be a wired or wireless connection, and the filtered electrical analog signal is conveyed to the analog-to-digital converter 118. The filtered electrical analog signal can be transferred from the band-pass signal filter to the analog-to-digital converter via a cloud-based storage medium. In some embodiments, the analog-to-digital converter is a high-resolution, sigma-delta analog-to-digital convener. Any other suitable, commercially available analog-to-digital converter can also be used in the embodiments of the present disclosure.

Still referring to FIG. 1, after the electrical analog signal passes through the signal conversion unit 112, a digital electrical signal is communicated through a connection 124 to a processing unit 126. Similar to the connections 110, 120, and 122, the connection 124 can be a wired or wireless connection, or any combination thereof, and the digital electrical signal can be conveyed to the processing unit 126. The digital electrical signal can be transferred from the analog-to-digital converter 118 to the processing unit 126 via a cloud-based storage medium. The processing unit 126, in the embodiment shown, includes a signal processor 128, a battery 130, and a physical memory 132. The processing unit includes more or fewer units in other embodiments, and the components of the processing unit are not required to be physically coupled or in close proximity and can exist as separate components.

In the embodiment shown, the signal processor 128 includes a personal computer (PC) used in combination with a digital signal processor (DSP) with a processor. Alternatively, a DSP can be used without a personal computer. The signal processor 128 is used to calculate approximate entropy, process, analyze, and classify acoustic signals, and provide results regarding the characteristics of the MPF, including a flow regime of the MPF. More detail on these calculations is provided as follows. In the embodiment shown, the signal processor 128 includes a user interface 134. Raw data, measurement results, characterizations of the MPF, and any other pertinent user input or signal processor output information is input by and displayed to a user on the user interface 134. One or more flow regimes of FIG. 5, described as follows, can be shown on the user interface 134.

The user interface 134 also is operable to accept user inputs to control the processing unit 126 and the system 100. The user interface, in some embodiments, includes audible and visual alerts, warnings, and alarms responsive to a MPF regime characterization. For example, if system 100 determined that MPF was in a slug flow when a slug flow was not acceptable for system 100, an audible and visual warning is provided to a user.

Figure 5:
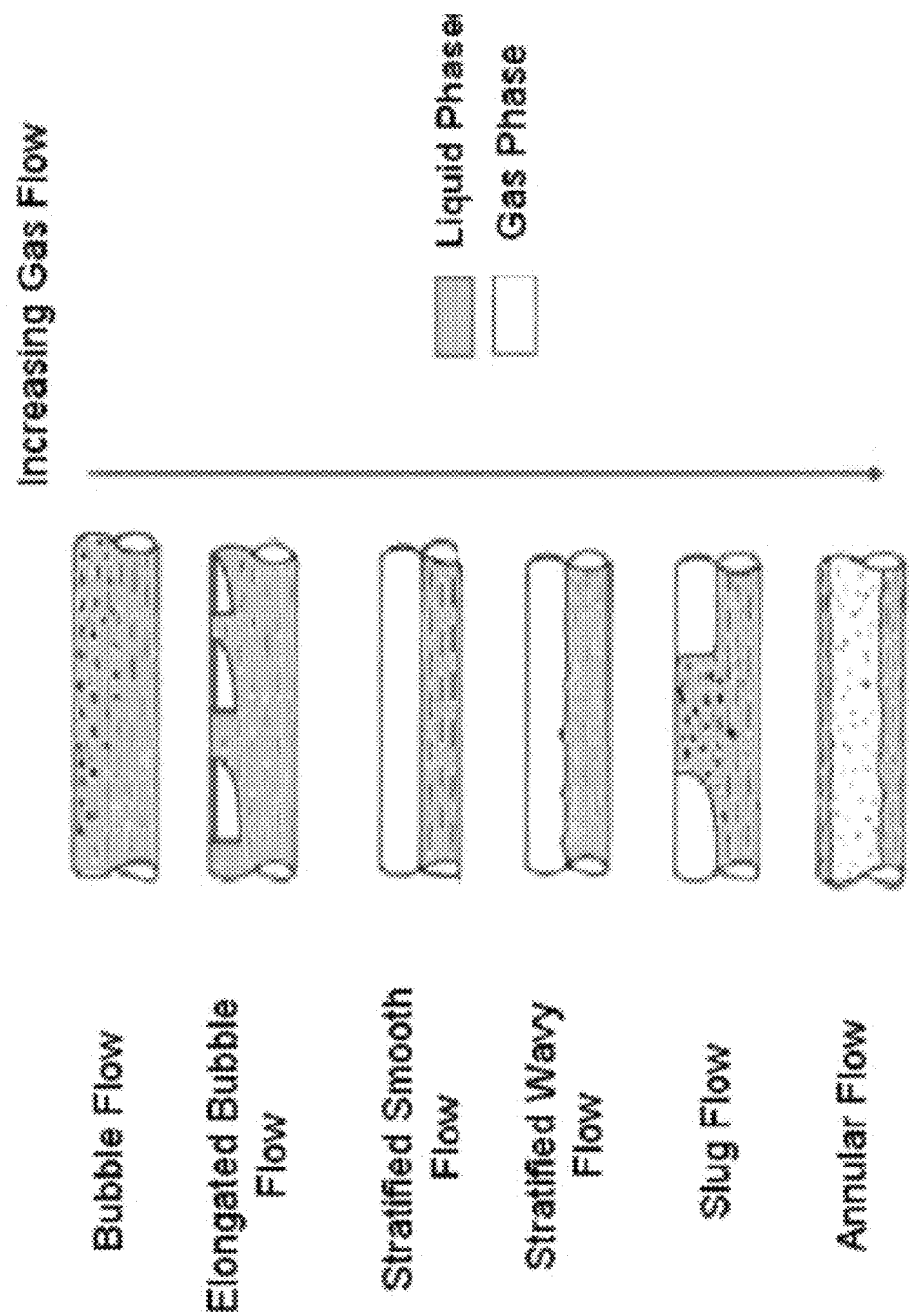
FIG. 5 is a graphical representation of multiphase fluid flow (MPF) regimes, optionally for display on a user interface according to an embodiment of the present disclosure.

The user interface 134 displays a graphical flow-type characterization such as those shown in FIG. 5. The system 100 accepts user input by the user interface 134 to change the flow regime, such as by controlling valves, actuators, and other means in the pipeline 102. Alternatively, the system 100 can act independently, i.e. without contemporaneous user input and based on pre-established rules and programs, to change the flow regime in the pipeline 102 if the current flow regime is unacceptable. Changing the MPF flow pattern is accomplished by controlling valves, actuators, and other means (not shown) in the pipeline 102. For example, if the system 100 determined that a MPF was in a slug flow when a slug flow was not acceptable for system 100 based on pre-established rules, the system 100 would act to change the MPF flow regime such as by controlling valves, actuators, and other means (not shown) in the pipeline 102.

The battery 130 is used to power the signal processor 128 and the physical memory 132. In other embodiments, more or fewer batteries are used. Any raw data, calculations, measurement results, and characterizations of the MPF can be saved in the physical memory 132. The physical memory 132 is communicable with the signal processor 128, and further stores executable steps to calculate approximate entropy and run a principal component analysis, both of which are discussed further as follows. The processing unit 126 can further be communicable with an optional external database 136, which can include further executable steps, programs, pre-determined values of MPF regimes, and any other input for or output of the processing unit 126.

In the embodiment of FIG. 1, the signal processor 128 is operable to calculate approximate entropy of the MPF responsive to the received digital signal. In statistics, approximate entropy (ApEn) is a technique used to quantify the amount of regularity and the unpredictability of fluctuations over time-series data. ApEn was introduced by Steven Pincus in 1991 in "Approximate entropy as a measure of system complexity," Proc. Natl. Acad. Sci. USA, Vol. 88, pp. 2297-2301, March 1991, Mathematics. This statistical method is used to quantify the complexity in noisy time series data. ApEn is robust and insensitive to artifacts or outliers, which means that infrequent, extremely small and infrequent, extremely large values have a small effect on the ApEn calculation. ApEn assigns a positive real number to a sequence of time-series of data, with larger values corresponding to greater apparent process randomness or irregularity, and smaller values corresponding to instances of more recognizable patterns in the data.

Different multiphase flow patterns will have different values of randomness and flow complexity, especially over shorter time periods, and these values of randomness and flow complexity are approximated using the ApEn technique.

In the embodiment of FIG. 1, the signal processor 128 in combination with the physical memory 132 performs the following steps. First, the received digital signal is segmented into short term, medium term, and long term time series. These time series from the digital signals are inputs for the ApEn algorithms described as follows. Next, for use in equations 1 and 2, positive real numbers are assigned to the time series, the positive real numbers including larger values and smaller values, the larger values corresponding to process randomness, and the smaller values corresponding to instances of recognizable patterns in the digital signal. Next, certain positive real numbers are categorized as outlier values. Following the preceding steps, using equations 1 and 2, the short term, medium term, and long term approximate entropy values are calculated for the MPF based upon the short term, medium term, and long term time series from the digital signal. For longer acoustic emission measurements, multiple ApEn values are calculated to compute average values for short, medium, and long term ApEn.

The algorithm for calculating ApEn for time series data is known and provided as follows. First, a time series of data would be obtained, such as from components 106 through 132 in FIG. 1. Such a time series of data can be represented by y(1), y(2), . . . , y(N), where N raw data values are measured at equally spaced time intervals. Next, an integer m, and a positive real number r are fixed, where m represents the length of the compared run of data, and r specifies the filtering level. Next, a sequence of vectors x(1), x(2), . . . , x(N−m+1) in $R^m$ is formed, and real m-dimensional space is defined by x(i)=[y(i), y(i+1), . . . , y(i+m−1)].

Following these steps, the sequence x(1), x(2), . . . , x(N−m+1) is used to construct for each i, where 1≤i≤N−m+1, $$C_i^m(r) = \frac{\text{number of } x(j) \text{such that } d[x(i), x(j)] < r}{N - m + 1},$$

where d[x, x']=$\max_a$|y(a)−y'(a)|.

The u(a) are the m scalar components of x. Here, d represents the distance between the vectors x(i) and x(j), given by the maximum difference in their respective scalar components.

Next, equation 1 is calculated using the elements described previously.

$$\Phi^m(r)=(N-m+1)^{-1}\Sigma_{i=1}^{N-m+1} \log(C_i^m(r)) \qquad \text{Eq. (1)}$$

Following the previous steps, approximate entropy is calculated according to equation 2.

$$\text{ApEn}=\Phi^m(r)-\Phi^{m+1}(r) \qquad \text{Eq. (2)}$$

For ApEn based MPF regime measurements and characterizations, a database of short, medium, and long term ApEn values that are representative of the respective MPF regime at various flow rates is developed. Such data can be acquired from laboratory flow loops and actual field tests. Data acquired from surface or downhole conditions can be used depending on the target application. Different databases can be developed for systems of different embodiments, such as the different embodiments of FIGS. 1-4. Initial characterization of the systems of the present disclosure can take place in a flow loop rather than a well or field application, but the flow loop data ideally should be representative of MPF regimes within a well or field application.

The MPF loop generally used in laboratory testing and qualification is closed circuit (as there is a loop). Individual flow rates of water, brine, oil, and gas can be varied to generate representative flow conditions for different wells and fields. A separator is used within a flow loop, in some embodiments, to separate the individual phases. The flow loops can also operate at greater temperatures and pressures, and the actual oil field conditions can be replicated in the lab.

Following the calculation of the ApEn values from the digital signal, these calculated short term, medium term, and long term ApEn values are compared to pre-calculated or pre-determined short term, medium term, and long term ApEn values in the physical memory 132 and, optionally, values in a similar database of pre-calculated values, such as the optional external database 136. Finally, characteristics of the MPF are determined responsive to similarities between the short term, medium term, and long term approximate entropy values for the MPF calculated from the digital signal and the pre-calculated short term, medium term, and long term approximate entropy values in the physical memory 132. After determination of the flow regime of the MPF, and other characteristics such as flow velocity (described further as follows with regard to FIG. 2), the calculations, results, and flow characterization are displayed on the user interface 134, which accepts user inputs to control the processing unit, and is operable to display the characteristics of the MPF to a user or operator of the system 100.

In the embodiments of the present disclosure, in order to characterize MPF responsive to acoustic emission detection, a system is initially characterized, optionally in a lab, to develop a detailed database containing ApEn values for a variety of flow regimes. In certain embodiments of the present disclosure, in order to initially characterize MPF in the system, the following steps for characterization can be carried out. Such steps enable the physical memory 132, or other databases communicable with the processing unit 126, to have a comprehensive series of values that can be used to characterize MPF flow regimes. The steps, in one embodiment, proceed as follows.

First, at either or both a lab and a field site, different MPF configurations are generated in an applicable pipeline configuration. For the different MPF configurations that are generated, different fractions of oil, water, gas, and solids should be used. These conditions, in some embodiments, are designed to substantially resemble expected actual MPF configurations during field applications in which MPF must be characterized according to systems and methods of the present disclosure. Next, a test matrix is defined where oil, water (or brine), and gas flow rates are varied accordingly. These conditions, in some embodiments, are designed to substantially resemble expected actual MPF configurations during field applications in which MPF must be characterized according to systems and methods of the present disclosure. Test matrices with the following conditions can be generated: (1) stepped values of watercut; (2) stepped values of total liquid flow; and (3) different MPF flow patterns, for example those shown in FIG. 5.

Following these steps, the ApEn is calculated for each of the test matrix data points. The ApEn is calculated using the algorithms provided previously. In one embodiment, the following entropy values can be calculated: (1) short term (S): about 1-10 seconds; (2) medium term (M): about 10-120 seconds; and (3) long Term (L): about 2-10 minutes. For each particular flow regime, at each test point in the test matrix, the resulting ApEn calculated values can be in the form of a range of a value, and not necessarily just a fixed number. By completing the steps of an initial flow characterization, a data set of ApEn values for different flow conditions is obtained and stored in a database such as, for example, the physical memory 132 in FIG. 1.

Referring now to FIG. 2, a schematic diagram of a correlation passive acoustic emissions based system 200, according to one embodiment of the present disclosure, is shown. Certain elements shown in FIG. 2 are also shown in FIG. 1 and described previously. In the embodiment of FIG. 2, in addition to the acoustic emission sensor 106 mounted to the segment 104 of the pipeline 102, a second acoustic emission sensor 107 is mounted to the segment 104 of the pipeline 102. As shown, the second acoustic emission sensor 107 is downstream of the acoustic emission sensor 106 in the Y1 direction; however, in other embodiments the second acoustic emission sensor 107 can be disposed upstream of the acoustic emission sensor 106 in the Y2 direction at a segment of the pipeline 102 operable to support MPF.

In FIG. 2, a connection 111, a signal conversion unit 113, a preamplifier 115, a band-pass signal filter 117, an analog-to-digital converter 119, and connections 121, 123, and 125 are shown. These units are similar, respectively, to the connection 110, the signal conversion unit 112, the preamplifier 114, the band-pass signal filter 116, the analog-to-digital converter 118, and the connections 120, 122, and 124 described previously. In some embodiments, components 113, 115, 117, 119, 121, 123, and 125 need not to be separate from components 112, 114, 116, 118, 120, 122, and 124. For example, the connection 111 proceeding from the second acoustic emission sensor 107 can simply connect the second acoustic emission sensor 107 to the signal conversion unit 112 and the other components.

In the embodiment of FIG. 2, the acoustic emission sensor 106 and the second acoustic emission sensor 107 are disposed a distance D apart. More than two acoustic emission sensors are used in other embodiments of the present disclosure. The pair of acoustic emission sensors 106, 107 is implemented to measure the flow velocity through the pipe. The acoustic emission sensors 106, 107 are placed relatively closely to one another such that the MPF pattern is coherent or similar as it passes both sensors. The relative closeness of the acoustic emission sensors 106, 107 to one another will vary depending, in part, on the geometry of the pipeline 102 and the physical properties of the liquid. The distance between the acoustic emission sensors 106, 107 can be about 1 meter, can be about 0.5 meters, or can be about 5 meters. If more than two acoustic emission sensors are used, the distance between the respective acoustic emission sensors can be the same or can be different. If one sensor is on a vertical section of casing and another is on a horizontal section of casing. D will be the flow distance between both sensors, and not the actual distance.

As the MPF progresses through the segment 104 of the pipeline 102, both of the acoustic emission sensors 106, 107 receive acoustic emissions of the MPF flow separated by the known distance D between them. If the MPF characteristics are coherent/substantially similar when measured at both of the acoustic emission sensors 106, 107, then the time for the fluid to travel between the acoustic emission sensors 106, 107 is calculated. For example, at some time $t_1$ the MPF passes the acoustic emission sensor 106 and at some time $t_2$, the MPF passes the second acoustic emission sensor 107. If the MPF flow characteristics are substantially the same at both points, a $\Delta t$ is calculated to determine velocity with $t_2 - t_1 = \Delta t$. In certain embodiments, by correlating the received raw acoustic emissions from both of the acoustic emission sensors 106, 107, and determining if both acoustic emissions are substantially the same, then the fluid velocity is provided by the equation velocity=$D/\Delta t$.

Therefore, the acoustic emission sensors 106, 107, when used in this way, provide an accurate estimate for fluid velocity along with MPF regime measurement. The distance D should be carefully designed, because if D is large or very small, the acoustic emission sensors 106, 107 will not see the same physical characteristics in the MPF regime, and the correlation between the acoustic emission sensors 106, 107 will not provide reliable measurement results. The fluid velocity through the segment 104 is calculated by the processing unit 126 and displayed on the user interface 134. The user interface 134 displays the real-time fluid flow characteristics including fluid velocity and is operable to display graphs comparing past flow characteristics with current flow characteristics, including flow velocity.

Figure 3:
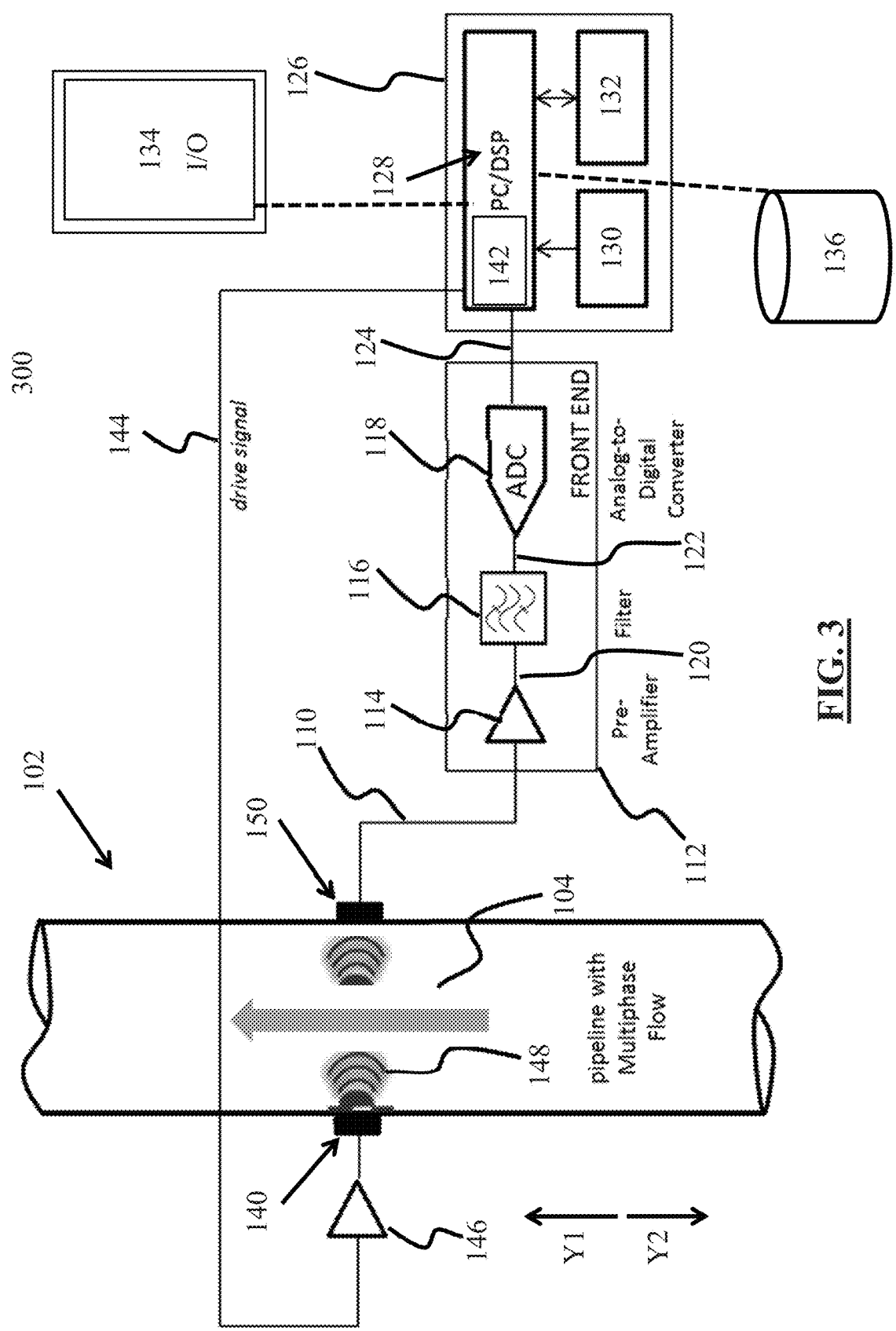
FIG. 3 is a schematic diagram of an active system according to an embodiment of the present disclosure.
Figure 4:
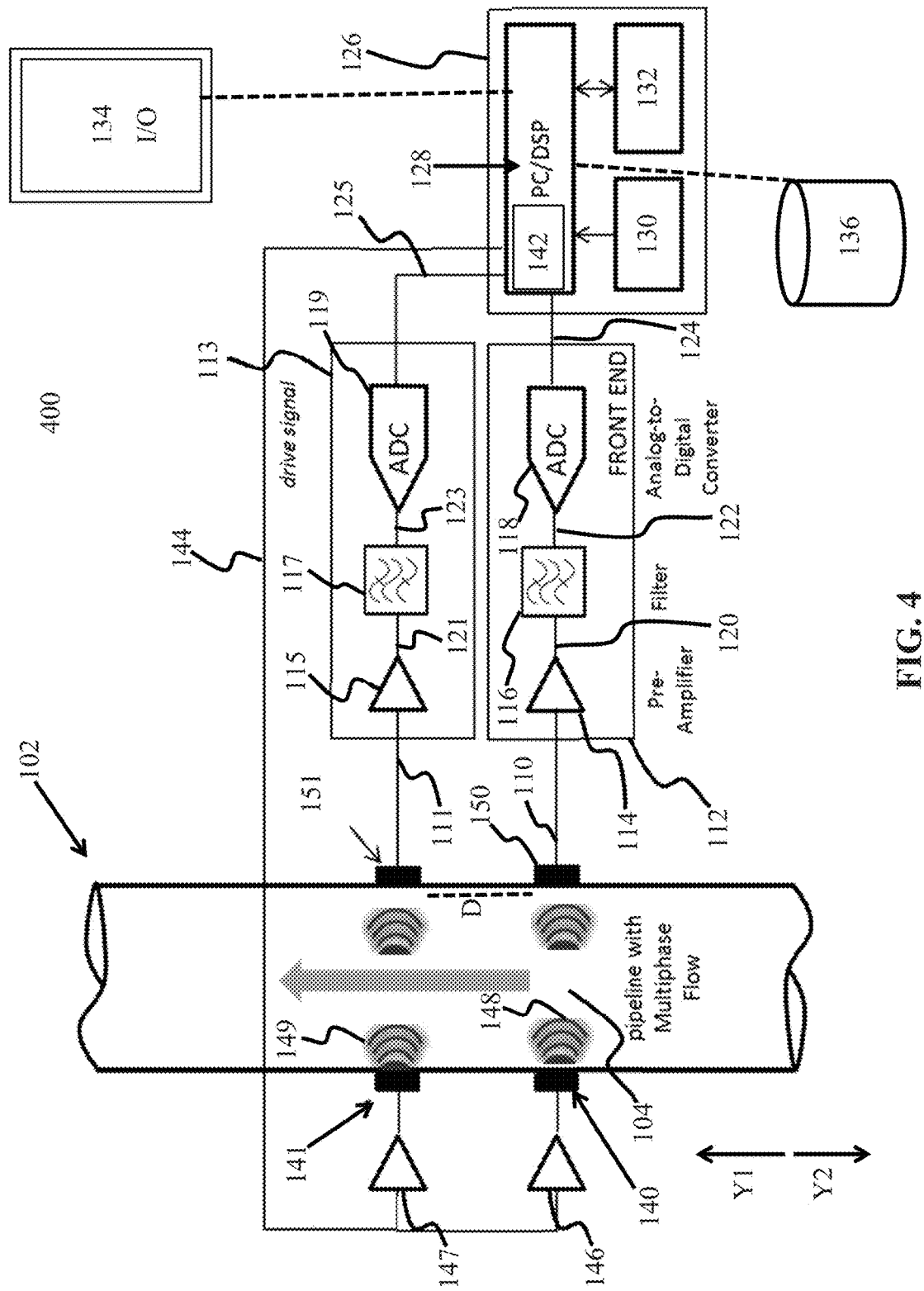
FIG. 4 is a schematic diagram of an active system according to an embodiment of the present disclosure.

Referring now to FIG. 3, a schematic diagram of an active acoustic transmission based system 300, according to one embodiment of the present disclosure, is shown. Certain components represented are numbered according to the embodiment of FIG. 1 and represent the same components described with reference to FIG. 1 previously. In the embodiment of FIG. 3, an acoustic transmitter 140 is mounted on the pipeline 102 proximate the segment 104 and is disposed substantially in line with an acoustic receiver 150. In the embodiments of FIGS. 3 and 4, the system configurations are "active." In active system configurations, one or more acoustic transmitters are used to transmit an acoustic signal of a fixed frequency through the MPF, and the acoustic signal is received by one or more acoustic receivers. Subsequent processing is performed on the received acoustic signal received by the acoustic receiver(s) to determine the MPF flow regime and other characteristics.

In some embodiments of the active systems described, the acoustic transmitters transmit an acoustic signal over a fixed acoustic frequency or within a narrow, pre-set band of frequencies. This fixed frequency (or narrow, pre-set band of frequencies) is receivable by the acoustic receiver for one or more of storage, transmission, and processing. The acoustic transmitter(s) and acoustic receiver(s) in the embodiments of the active systems have similar transducer properties including, but not limited to, operating frequency, bandwidth, sensitivity, and beam angle.

In the embodiment of the system of FIG. 3 (and FIG. 4), the acoustic transmitter 140 and the acoustic receiver 150 are in direct contact with the MPF. The acoustic transmitter 140 and the acoustic receiver 150 are mounted in fitted holes bored in the segment 104 of pipeline 102, such that a transmitting surface of the acoustic transmitter 140 and a receiving surface of the acoustic receiver 150 are in direct contact with the MPF. The components 140, 150 are mounted in this configuration so that the acoustic energy effectively propagates from the acoustic transmitter 140 through the MPF to the acoustic receiver 150.

The acoustic transmitter 140 and the acoustic receiver 150 operate at a fixed high frequency, in the range of about 0.5 MHz to about 2 MHz. The acoustic transmitter 140 and the acoustic receiver 150 are operated at a narrow beam angle, in the range of about 5° to about 15°. In the embodiment of FIG. 3, the processing unit 126 further includes a signal generator unit 142 within signal processor 128. The signal generator unit 142 is operable and controllable by the user interface 134 to provide a drive signal 144 to the acoustic transmitter 140. In some embodiments, the signal generator unit generates a continuous sine wave signal of a high frequency, in the range of about 0.5 MHz to about 2 MHz. In other embodiments, however, other signals are generated by the signal generator unit.

The drive signal for the acoustic transmitter 140, in the embodiment of FIGS. 3 and 4, can be modified and can be a continuous sine wave or a square wave with a frequency equal to the operating frequency of the acoustic transmitter 140 and the acoustic receiver 150. The amplitude of the signal is in the range of about 5 to about 10 volts (V). The drive signal can be generated using a built-in oscillator in any commercial digital signal processor (DSP) or microcontroller (MCU).

The drive signal 144 is amplified, in the embodiment shown, by an operational amplifier 146 prior to being conveyed to the acoustic transmitter 140. In other embodiments, no operational amplifier is required. The operational amplifier 146 is a high-voltage amplifier operable to about 50 volts (V) to about 100 V. The amplified signal is provided to drive the acoustic transmitter 140. Once the acoustic transmitter 140 receives an amplified drive signal from the operational amplifier 146, the acoustic transmitter 140 converts the electrical drive signal to an acoustic signal 148. The acoustic signal 148 output by the acoustic transmitter 140 can be a continuous signal. In some embodiments, the acoustic signal is of a high frequency, from about 0.5 MHz to about 2 MHz.

The acoustic signal 148 from the acoustic transmitter 140 travels through the MPF in the segment 104 of the pipeline 102 and is received by the acoustic receiver 150. The amplitude and energy of the received signal at a particular time depends on the exact composition of the MPF at that time. The acoustic receiver 150 receives the acoustic signal 148 and converts it to an electrical signal, in the embodiment shown an electrical analog signal. Similar to as previously described with regard to FIG. 1, the received signal is preamplified by the preamplifier 114 within the signal conversion unit 112. The received signal consists of actual signal as well as acoustic noise from the flow or the pipeline. After the preamplifier 114, the signal passes through the band-pass signal filter 116, the analog-to-digital converter 118, and into the processing unit 126. The signal processor 128 computes the energy of the received signal (see equation 3 as follows) and calculate the approximate entropy as described previously. Then, the signal processor 128 analyzes and classifies the acoustic signals to provide and display the metering results of the MPF characteristics and flow regime.

The calculated results, along with raw data received by the acoustic receiver 150, is stored in the physical memory 132 and displayed using the user interface 134. Any data within the processing unit 126 can be conveyed, stored, and displayed at a remote location using any one of or any combination of wired and wireless communications such as wireless internet and Bluetooth technology.

Referring now to FIG. 4, a schematic diagram of a correlation active acoustic transmission based system 400, according to one embodiment of the present disclosure, is shown. Certain elements shown in FIG. 4 are also shown in FIGS. 1-3 and described previously. In the embodiment of FIG. 4, in addition to the acoustic receiver 150 mounted to the segment 104 of the pipeline 102, a second acoustic receiver 151 is mounted to the segment 104 of the pipeline 102. As shown, the second acoustic receiver 151 is downstream of the acoustic receiver 150 in the Y1 direction; however, in other embodiments the second acoustic receiver 151 can be disposed upstream of the acoustic receiver 150 in the Y2 direction at a segment of the pipeline 102 operable to support MPF.

In FIG. 4, a connection 111, a signal conversion unit 113, a preamplifier 115, a band-pass signal filter 117, an analog-to-digital converter 119, and connections 121, 123, and 125 are shown. These units are similar, respectively, to the connection 110, the signal conversion unit 112, the preamplifier 114, the band-pass signal filter 116, the analog-to-digital converter 118, and the connections 120, 122, and 124 described previously. In some embodiments, components 113, 115, 117, 119, 121, 123, and 125 need not to be separate from components 112, 114, 116, 118, 120, 122, and 124. For example, the connection 111 proceeding from the second acoustic receiver 151 can simply connect the second acoustic receiver 151 to the signal conversion unit 112 and the other components.

In the embodiment of FIG. 4, in addition to the acoustic transmitter 140 mounted to the segment 104 of the pipeline 102, a second acoustic transmitter 141 is mounted to the segment 104 of the pipeline 102. As shown, the second acoustic transmitter 141 is downstream of the acoustic transmitter 140 in the Y1 direction; however, in other embodiments the second acoustic transmitter 141 can be disposed upstream of the acoustic transmitter 140 in the Y2 direction at the segment of the pipeline 102 operable to support MPF.

The acoustic transmitters 140, 141 and the acoustic receiver 150, 151 operate at a fixed high frequency, in the range of about 0.5 MHz to about 2 MHz. The acoustic transmitters 140, 141 and the acoustic receivers 150, 151 are operated at a narrow beam angle, in the range of about 5° to about 150. In the embodiment of FIG. 4, the processing unit 126 further includes a signal generator unit 142 within the signal processor 128. The signal generator unit 142 is operable and controllable by the user interface 134 to provide a drive signal 144 to the acoustic transmitters 140, 141. The signal generator unit 142 generates a continuous sine wave signal of a high frequency, in the range of about 0.5 MHz to about 2 MHz. In other embodiments, however, other signals can be generated by the signal generator unit.

The drive signal 144 is amplified by the operational amplifier 146 and a second operational amplifier 147 prior to being conveyed to the acoustic transmitters 140, 141, respectively. In other embodiments, no operational amplifiers are required. The operational amplifiers 146, 147 are high-voltage amplifiers operable to about 50 V to about 100 V. The amplified signal is provided to drive the acoustic transmitters 140, 141. Once the acoustic transmitters 140, 141 have received an amplified drive signal from the operational amplifiers 146, 147, respectively, the acoustic transmitters 140, 141 convert the electrical signal to acoustic signals 148, 149. The acoustic signals 148, 149 output by the acoustic transmitters 140, 141 are continuous signals. In some embodiments, the acoustic signals are of a high frequency, from about 0.5 MHz to about 2 MHz.

The acoustic signals 148, 149 from the acoustic transmitters 140, 141 travel through the MPF in the segment 104 of the pipeline 102 and are received by the acoustic receivers 150, 151, respectively. The amplitude and energy of the received signals at a particular time depends on the exact composition of the MPF at that time. The acoustic receivers 150, 151 receive the acoustic signals 148, 149 and convert them to an electrical analog signal. Similar to as previously described with regard to FIG. 1, the received signals are preamplified by the preamplifiers 114, 115 within the signal conversion units 112, 113, respectively. The received signals consist of actual, useful signal as well as acoustic noise from the MPF, the pipeline, and the environment surrounding the pipeline. After the preamplifiers 114, 115, the signals pass through the band-pass signal filters 116, 117, the analog-to-digital converters 118, 119, and into the processing unit 126. The signal processor 128 computes the energy of the received signals and calculate the approximate entropy as described previously. Then, the signal processor 128 analyzes and classifies the acoustic signals to provide and display the metering results of the MPF characteristics and flow regime.

The calculated results, along with raw data received by the acoustic receivers 150, 151 are stored in the physical memory 132 and displayed using the user interface 134. Any data within the processing unit 126 can be conveyed, stored, and displayed at a remote location using any one of or any combination of wired or wireless communications such as wireless internet and Bluetooth technology.

In the embodiment of FIG. 4, the acoustic receiver 150 and the second acoustic receiver 151 are disposed a distance D apart. More than two acoustic receivers can be used in other embodiments of the present disclosure. A pair of acoustic receivers 150, 151 is implemented to measure the flow velocity through the pipe. The acoustic receivers 150, 151 are placed relatively closely to one another such that the MPF pattern is coherent or similar as it passes both sensors. The relative closeness of the acoustic receivers 150, 151 to one another will vary depending, in part, on the geometry of the pipeline 102 and the physical properties of the liquid. The distance D between the acoustic receivers 150, 151 can be about 1 meter, or about 0.5 meters, or about 5 meters. If one sensor is on a vertical section of casing and another is on a horizontal section of casing, D will be the flow distance between both sensors, and not the actual distance.

As the MPF progresses through the segment 104 of the pipeline 102, both of the acoustic receivers 150, 151 receive the acoustic signals 148, 149 from the acoustic transmitters 140, 141, respectively, through the MPF flow. The acoustic receivers 150, 151 are separated by the known distance D between. If the MPF characteristics are coherent/substantially similar when measured at both of the acoustic receivers 150, 151, then the time for the fluid to travel between the acoustic receivers 150, 151 is calculated. For example, at some time $t_1$ the MPF passes the acoustic receiver 150 and at some time $t_2$, the MPF passes the second acoustic receiver 151. If the MPF flow characteristics are substantially the same at both points, a $\Delta t$ is calculated to determine velocity as $t_2 - t_1 = \Delta t$. In certain embodiments, by correlating the received raw signals at both of the acoustic receivers 150, 151 from the acoustic transmitters 140, 141, respectively, and determining if both signals are substantially the same, then the fluid velocity is provided by the equation velocity=$D/\Delta t$.

Therefore, the acoustic receivers 150, 151, when used in this way, provide an accurate estimate for fluid velocity along with MPF regime measurement. The distance D should be carefully designed, because if D is large or very small, the acoustic receivers 150, 151 will not see the same physical characteristics in the MPF regime, and the correlation between the acoustic receivers 150, 151 will not provide reliable measurement results. The fluid velocity through the segment 104 is calculated by the processing unit 126 and displayed on the user interface 134.

Referring now to FIGS. 3 and 4, for the active acoustic transmission based system 300 and the correlation active acoustic transmission based system 400, the following steps are used, in one embodiment, to operate the systems in such a way as to accurately measure, calculate, and determine the characteristics and flow regime of a MPF. First, the acoustic transmitter 140 is activated with the acoustic receiver 150. In the embodiment of FIG. 4, the second acoustic transmitter 141 and the second acoustic receiver 151 would also be activated. Next, the acoustic signal received by the acoustic receiver 150 is pre-amplified by the preamplifier 114, filtered by the band-pass signal filter 116 and converted into a digital signal by the analog-to-digital converter 118. In the embodiment of FIG. 4, the acoustic signal received by the second acoustic receiver 151 is pre-amplified by the preamplifier 115, filtered by the band-pass signal filter 117 and converted into a digital signal by the analog-to-digital converter 119.

Next, the digital signal is acquired by the processing unit 126 and the signal processor 128. The signal processor 128 can calculate the energy. $E_s$, of a received acoustic signal, x(n), using equation 3, shown as follows:

$$E_S = \sum_{-\infty}^{\infty} |x(n)|^2 \qquad \text{Eq. (3)}$$

For a finite number of samples N, equation 3 can be re-written as equation 3a:

$$E_S = \sum_{n=0}^{N} |x(n)|^2 \qquad \text{Eq. (3a)}$$

In some embodiments, energy is computed for every 1000 cycles of received signal. For example, if the systems 300 and 400, including the acoustic transmitter(s) and the acoustic receiver(s), are operating at 1 MHz, energy will be computed for every 1000 cycles, which is equal to 1000 energy measurements per second. Using this example, if the received signal is sampled at a sampling frequency $f_s$, the number of samples N will be equal to equations 3b and 3c shown as:

$$N = \frac{1}{\text{acoustic freqeuncy}} \times f_s \times \text{Number of cycles} \qquad \text{Eq. (3b)}$$

$$N = \frac{1}{10^6} \times f_s \times 1000 Eq. \qquad (3c)$$

The signal processor 128 segments the acoustic energy signal(s) into short, medium, and long term time series. These time series signals will be inputs for the ApEn algorithm, as described previously with regard to FIG. 1. ApEn values are calculated for each time series. For longer acoustic emission measurements, multiple ApEn values will be calculated to compute average values for short, medium, and long term ApEn. The computed values of short, medium, and long term ApEn can be searched in the corresponding physical memory 132 and optional external database(s), such as the optional external database 136, which include pre-calculated (pre-determined) ApEn values to provide the MPF measurement result. In the embodiment of FIG. 4, cross correlating acoustic transmitter/receiver pairs 140, 150 and 141, 151 provide an estimate for fluid velocity through the segment 104 and the pipeline 102.

Referring now to the systems of FIGS. 3-4, in certain embodiments, units such as the acoustic receivers 150, 151 and the acoustic transmitters 140, 141 can be clamped on the outside of a pipeline, such as the pipeline 102, using a couplant between the units' surfaces and the pipeline 102. Clamping components only on the outside of the pipeline results in a non-invasive system. In such a system, some of the acoustic signals will propagate through the MPF, while some of the acoustic signals will propagate through the pipeline. The portion of acoustic signal that propagates through the pipeline is referred to as the lamb wave. Signal processing techniques are required to separate the lamb waves from useful signal travelling through the MPF. These signal processing techniques are executable on the signal processor 128. The separated acoustic signal is processed using the same ApEn techniques as described earlier.

In some embodiments, passive systems of the present disclosure, such as those shown in FIGS. 1 and 2 and described previously, use acoustic emission sensors mounted on the outside or exterior of a pipe to create a non-invasive characterization system, optionally with the use of a couplant. In some embodiments, active systems of the present disclosure, such as those shown in FIGS. 3 and 4 and described previously, use acoustic transmitters and acoustic receivers that are in direct contact with the MPF. The acoustic transmitters and acoustic receivers are mounted in fitted holes bored in a portion of a pipeline, such that a transmitting surface of the acoustic transmitters and a receiving surface of the acoustic receivers are in direct contact with the MPF. In some embodiments, the components are mounted in this configuration so that the acoustic energy effectively propagates from the acoustic transmitters through the MPF to the acoustic receivers.

In some embodiments, if the acoustic transmitter and acoustic receiver units are mounted to be in direct contact with the MPF, the processing of the received signal will be computationally less expensive, as there is no lamb wave received by the acoustic receiver. In some embodiments, if the acoustic transmitter and acoustic receiver units are mounted exterior to the pipe, a significant portion of the transmitted acoustic signals will propagate through the pipeline wall to the acoustic receiver without travelling through the MPF (lamb waves). Signal processing techniques are required to separate the lamb waves from the received signal that has traveled through the MPF, which may result in more complex signal processing and computation. The advantage of such a system, however, is the non-invasive nature of the acoustic transmitter and acoustic receiver units, as they can be deployed anywhere on a pipeline just by clamping the acoustic transmitter and acoustic receiver units on the pipeline along with all other electronics and processing units external to the pipeline.

The undesirable lamb waves can be treated as a continuous noise signal, because a continuous acoustic signal is transmitted by the acoustic transmitter(s). The lamb wave noise signal will have the same frequency as the actual signal, but a different amplitude and phase, depending in part on the pipe wall through which it is travelling. This lamb wave noise signal can be characterized (for example in the laboratory) and removed from the received signal in the processing unit, in the band-pass signal filter, or by the acoustic receiver by setting a specific frequency.

The systems of FIGS. 1-4 can be deployed on surface pipelines and facilities. The systems can be deployed on wellheads and can also be deployed downhole, inside a wellbore for MPF regime measurement from wellbores. The systems can be a part of a permanent smart completion, or a retrievable system in mother bore or laterals. Permanent smart completions incorporate permanent downhole sensors, flow measurement devices, and surface-controlled downhole flow control valves, enabling the monitoring, evaluation, and active production (or injection) management in real-time without any well interventions. Data are transmitted to the surface for local or remote monitoring. These systems are permanently deployed for the complete life of a well.

A retrievable system is a wireline or coiled tubing deployable system that is lowered into the well for a limited amount of time to perform specific measurements or logging operations. The system is retrievable from the well once the desired operation has been performed.

In some embodiments of the systems of FIGS. 1-4, the systems can be integrated with one or more sensor measurements (including single or differential pressure measurements) to improve the accuracy of data and MPF calculations. Additionally, any one of or any combination of temperature sensors, pressure sensors, accelerometers, densimeters, and flow meters is contemplated for use in the systems and methods of the present disclosure. Measurements from such devices are provided by wired or wireless means to the processing unit 126 and displayed on the user interface 134.

In certain embodiments of the systems of FIGS. 1-4, the electronic units such as, for example, the acoustic emission sensor 106, the preamplifier 114, the band-pass signal filter 116, the analog-to-digital converter 118, the processing unit 126, the signal processor 128, the battery 130, the physical memory 132, and the user interface 134 and any suitable, required processing circuitry of the systems can be combined in a single system responsive to Application Specific Integrated Circuit (ASIC) and System-on-Chip (SoC) methodologies. In these embodiments, for example, a very compact system can be developed. Such a system with proper protective packaging would be suitable for harsh environments faced in downhole deployments inside a well.

Referring now to FIG. 5, a graphical representation is shown of MPF regimes, optionally for display on the user interface 134 in an embodiment of the present disclosure. While other flow regimes are measured and characterized by the systems of FIGS. 1-4, FIG. 5 provides certain flow graphics that are useful to an operator of the systems. Bubble flow is characterized by small gas bubbles flowing along the top of the pipe. Elongated bubble flow is characterized by collisions between the individual bubbles occurring more frequently with increasing gas flow rate and coalescing into elongated "plugs." This is often called plug flow. Stratified smooth flow is characterized by gas plugs coalescing to produce a continuous gas flow along the top of the pipe with a smooth gas-liquid interface typical of stratified flow at relatively low flow rates. Stratified wavy flow is characterized by the gas-liquid interface being rarely smooth with ripples appearing on the liquid surface. In this embodiment, the amplitude increases with increased gas flow rate.

Slug flow is characterized by the amplitude of the waves travelling along the liquid surface becoming sufficiently large enough for them to bridge the top of the pipe, and thus the flow enters the slug flow regime. In this embodiment, the gas flows as intermittent slugs with smaller bubbles entrained in the liquid. Annular flow is characterized by the gas flow rate being large enough to support the liquid film around the pipe walls. Liquid is also transported as droplets distributed throughout the continuous gas stream flowing in the center of the pipe. The liquid film is thicker along the bottom of the pipe because of the effect of gravity.

As noted previously, acoustic emissions from MPF are dependent upon, in part, gas bubble formation and cavitation, regime breakage and coalescence, and interaction of various phases within a multiphase flow. These characteristics vary for different MPF regimes, flow rates, and also for different relative amounts of liquid, gas/vapor, and solids in the MPF. The systems and methods of the present disclosure surprisingly and unexpectedly are able to accurately and efficiently characterize flow regimes, such as, for example, those in FIG. 5, by applying the ApEn calculations to remove unwanted acoustic noise and outlier measurements, which have prevented the accuracy of such systems and methods.

In other embodiments of the systems of FIGS. 1 and 2, principal component analysis (PCA) is applied to optimize the systems. The systems of FIGS. 1 and 2 are considered passive systems, at least in part because there are no added acoustic transmitters. The acoustic emissions received by the acoustic emission sensors 106, 107 would arise largely from the MPF, the pipeline 102, and the local environment surrounding the acoustic emission sensors 106, 107. Initially, in the systems of FIGS. 1 and 2, the acoustic emission sensors 106, 107 can be broadband acoustic emission sensors operable to gather data including broadband frequency emissions from the MPF, the pipeline 102, and the surrounding environment. The data acquired by such broadband acoustic emission sensors is gathered in any one of or any combination of a field application, such as in-situ in a well or with a pipeline, and in a lab setting in a closed flow loop with tight controls on flow characteristics. In one embodiment, while such data is being gathered, the appropriate Reynolds number is known for the MPF for which data is being gathered.

With the data gathered, Lime series of acoustic waveforms are formed, and by performing a Fourier Transformation on the data, the data is converted into measurements of acoustic power as a function of frequency. After the Fourier transformation, a suite of measurements is performed using a test matrix including different conditions of the MPF including, but not limited to, stepped values of watercut, stepped values of total liquid flow, and different multiphase flow patterns, such as, for example, those shown in FIG. 5. Once a full dataset has been gathered, the data is post processed using PCA on the dataset. PCA is a multivariate method that is optimal for handling co-linearity, and is described in detail in Nørgaard, L. et al., "Principal Component Analysis and Near Infrared Spectroscopy," A white paper from FOSS. In order to calculate a PCA model, several different algorithmic approaches can be applied. Several of these are implemented in commercial software packages that offer the possibility to both calculate and present results from a PCA model.

In other words, PCA makes it possible to determine what variables are most important for accurately determining a system characteristic. A pipeline, such as the pipeline 102, will emit various acoustic emissions at various frequencies over time, especially if there is a MPF proceeding through the pipeline 102. The acoustic emission sensor, such as acoustic emission sensor 106, receives and records all of these acoustic emissions in situations in which the acoustic emission sensor is a broadband acoustic emission sensor. In some embodiments of the systems and methods described, however, not all acoustic emissions received by the acoustic emission sensor(s) are pertinent to the determination of MPF characteristics and flow regime. For example, certain frequencies change in a system, but the flow characteristics and the flow regime of a MPF may not. In such a case, the systems and methods of the present disclosure would not want to interpret such a change in frequency as having an effect on MPF characteristics or the MPF regime.

Therefore, once a full dataset has been gathered from one or more broadband acoustic emission sensors, the dataset is post-processed by performing PCA on the dataset. PCA will, in some embodiments, identify the linear combination of key frequencies which are used to approximate a score which correlates or clusters resulting values into separable classifications. In turn, this will also identify which frequencies are less significant than others. Furthermore, such a process of PCA allows for certain hardware optimization and cost savings. For example, broadband acoustic emission sensors can be replaced with an array of less expensive single frequency tuned receivers where the frequencies are in line with the values output from the PCA analysis. This can reduce system cost and computational overhead, because the tuned receivers are acting as band-pass signal filters which are only looking at the significant points of the measurement.

In order to calculate a PCA model, several different algorithmic approaches can be applied. Several of these are implemented in commercial software packages that offer the possibility to both calculate and present results from a PCA model. In other embodiments, a system can be implemented with a broadband receiver, and then a series of parallel band-pass signal filters can be implemented in hardware or using digital signal processing techniques, tuned towards the significant frequencies identified by the PCA approach.

Figure 6:
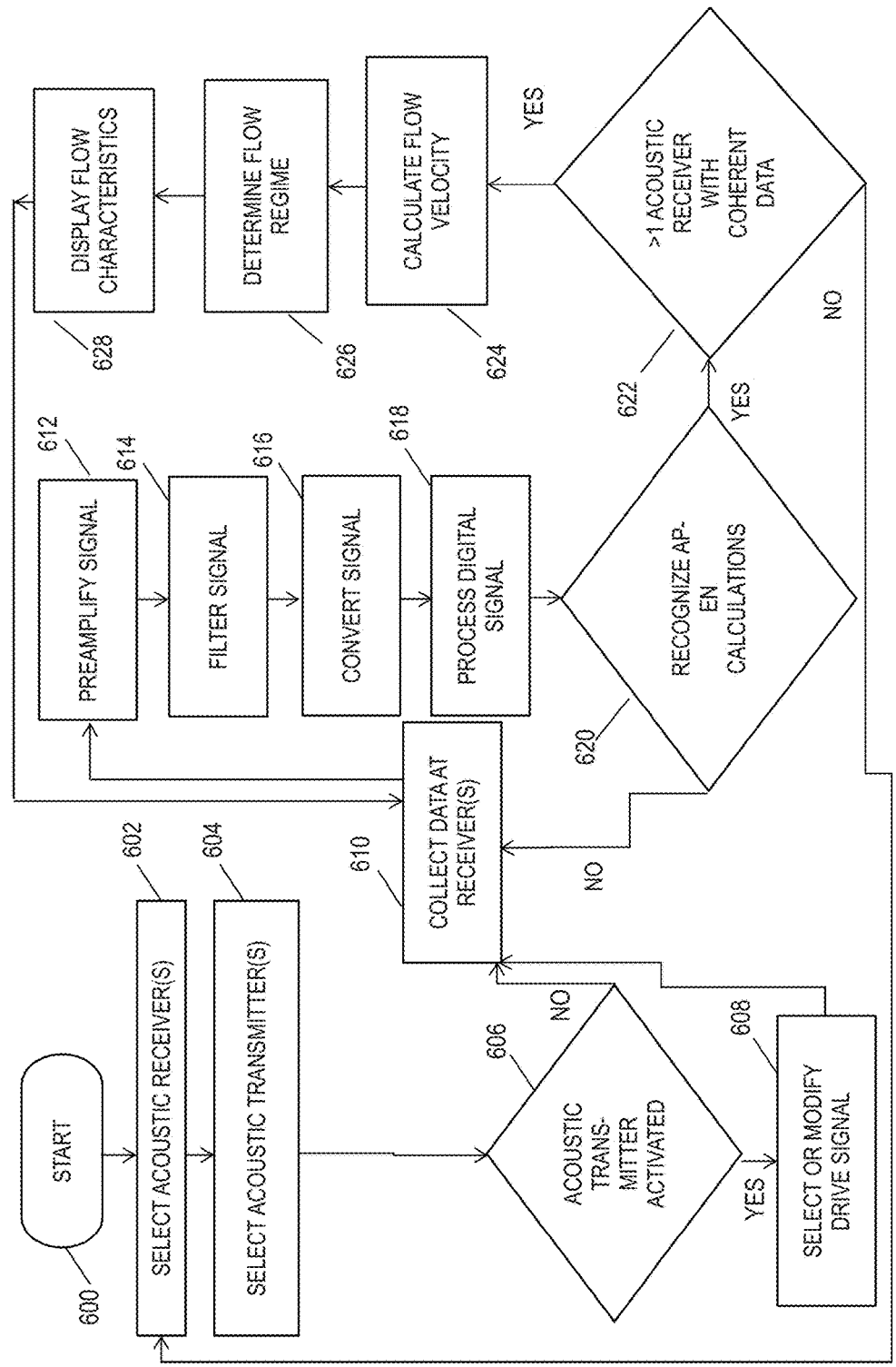
FIG. 6 is a flow chart for a method according to an embodiment of the present disclosure.

Referring now to FIG. 6, a flow chart for an embodiment for a method of operation of the system of FIG. 4, is provided. Similar methods of operations can be used in other embodiments of the systems presented. Starting at step 600, one or more users or operators of the system 400 can be prompted by the user interface 134 to start the system 400. Such a prompt can include audible and visual prompting, and the user or operator can be required to affirmatively start the system, or the system can start without an affirmative response from the user or operator. A suitable affirmative response from a user or operator might include actuating any one of or any combination of a button, switch, and lever, touching a touchscreen, and responding by voice to a user interface operable to accept voice commands. The user interface 134 and the processing unit 126 are operable to operate with remote devices such as, for example, laptop computers and smart phones through wired or wireless networks, devices, or communication schemes, as will be understood by those skilled in the art. Thus, the selections made by a user or operator described can be made remotely.

At step 600, the flow through the pipeline 102 can already be engaged, and can optionally already be flowing in a MPF regime. In some embodiments, however, the flow through the pipeline need not be engaged when the system is started and the flow through the pipeline need not be engaged at the same time the system is started. The flow through the pipeline 102 can be stopped, started, increased, or decreased at any point in the method of operation of FIG. 6 through any one of or combination of valves, stops, actuators, and similar devices known in the art. The flow chart for the method of operation shown in FIG. 6, in some embodiments, is completely automated within the processing unit 126, and step 600 for starting the system 400 arises responsive to the conditions of the system 400, without contemporaneous user input.

At step 602, the user interface 134 can prompt the user or operator to activate any one of or both of the acoustic receiver 150 and the second acoustic receiver 151. At step 604, the user interface 134 can prompt the user or operator to activate any one of or both of the acoustic transmitter 140, and the second acoustic transmitter 141. In certain embodiments of the system 400, the selection for one or more acoustic receivers and one or more acoustic transmitters is made by the system 400 responsive to system characteristics, such as, for example, the pipeline and system design, operating conditions, flow conditions, and past recorded measurements of the system 400.

At step 606, the system 400 operates to determine if one or more of the acoustic transmitters 140, 141 have been activated. If the system 400 determines that one or more of the acoustic transmitters 140, 141 have been activated, then at step 608 the system provides the user or operator the opportunity to select or modify the drive signal 144. The signal generator unit 142 is operable and controllable by the user interface 134 to provide a drive signal 144 to one or both of the acoustic transmitters 140, 141. In some embodiments, the signal generator unit generates a continuous sine wave signal of a high frequency, for example in the range of about 0.5 MHz to about 2 MHz. In other embodiments, however, other signals at other frequencies are generated by the signal generator unit after selection by a user or operator on the user interface.

At step 610, the system 400 begins to collect data at the one or more acoustic receivers that have been activated by the user. It is to be noted that the acoustic receivers 150, 151 can be operable to receive frequencies from only the acoustic transmitters 140, 141, from only the MPF, or from both the acoustic transmitters 140, 141 and the MPF. This can be done using any one of or combination of cut-off frequencies and set-frequency band-pass signal filters.

After the one or more acoustic receivers 150, 151 begin collecting data through one or more acoustic signals, the one or more signals is preamplified at step 612, filtered at step 614, and converted from an analog electrical signal to a digital signal at step 616. These steps are optionally carried out in the units of the signal conversion units 112, 113, described previously.

At step 618, the digital signal is processed in the processing unit 126, which includes the signal processor 128 and the physical memory 132. The digital signal is processed to calculate the approximate entropy of short term, medium term, and long term data series collected from any one of or any combination of the acoustic receivers 150 and 151. At step 620, the signal processor 128 determines if the approximate entropy calculations are recognized or comparable to pre-calculated or pre-determined approximate entropy values contained in any one of or any combination of databases and the physical memory 132. If the ApEn values of the measured signal are not recognizable, the system will continue to collect data at the acoustic receivers 150, 151.

At step 622, the system determines if there is greater than one acoustic receiver activated with the greater than one acoustic receiver receiving coherent data, or data showing that a MPF with similar characteristics is passing by the greater than one acoustic receivers. If this is not true, then the user or operator is given the option to once again select the acoustic receiver before the system calculates flow velocity at step 624. If there is more than one operating acoustic receiver, and the data being retrieved at both sensors is coherent, then the flow velocity within the segment 104 of the pipeline 102 is calculated at step 624.

Next at step 626, the system 400 determines the flow regime in response to the ApEn calculations and the flow velocity. In other embodiments, the flow velocity is not needed and is not used in determining the flow regime, such as, for example, in the embodiment of the system 100 in FIG. 1 and the system 300 in FIG. 3. The flow regime can be determined and approximated to one of the flow regimes shown in FIG. 5 and described previously, or can be determined and approximated to a combination of any one of these regimes.

In other embodiments, the flow regime is determined to be some other flow regime responsive to the acoustic signals received by the acoustic receivers. After the flow regime is determined, the flow characteristics are displayed to a user or operator by the user interface 134 at step 628. While in the embodiments of FIGS. 1-4 the user interface 134 is shown to be a component of the processing unit 126, the user interface 134 can be a separate unit coupled by wired or wireless communication to the processing unit 126, such as a smart phone or laptop computer.

Thus, a user or operator can receive displayed flow characteristics remotely and in real-time, separate from the system 400. The user or operator also can control the systems remotely by input into the user interface 134. At step 628, other real-time data is also displayed on the user interface 134 not calculated in the system 400, but obtained from other meters and means such as, for example, flow meters, thermal measurement devices, densimeters, accelerometers, and similar devices known in the art.

In the various embodiments of the disclosure described, a person having ordinary skill in the art will recognize that various types of memory are readable by a computer, such as the memory described in reference to the various computers and servers, e.g., computer, computer server, web server, or other computers with embodiments of the present disclosure.

The singular forms "a," "an," and "the" include plural referents, unless the context clearly dictates otherwise.

Examples of computer-readable medium can include but are not limited to: one or more nonvolatile, hard-coded type media, such as read only memories (ROMs), CD-ROMs, and DVD-ROMs, or erasable, electrically programmable read only memories (EEPROMs); recordable type media, such as floppy disks, hard disk drives, CD-R/RWs, DVD-RAMs, DVD-R/RWs, DVD+R/RWs, flash drives, memory sticks, and other newer types of memories: and transmission type media such as digital and analog communication links. For example, such media can include operating instructions, as well as instructions related to the systems and the method steps described previously and can operate on a computer. It will be understood by those skilled in the art that such media can be at other locations instead of, or in addition to, the locations described to store computer program products, e.g., including software thereon. It will be understood by those skilled in the art that the various software modules or electronic components described previously can be implemented and maintained by electronic hardware, software, or a combination of the two, and that such embodiments are contemplated by embodiments of the present disclosure.

In the drawings and specification, there have been disclosed embodiments of methods, systems, and non-transitory computer-readable medium having stored computer programs of the present disclosure, and although specific terms are employed, the terms are used in a descriptive sense only and not for purposes of limitation. The embodiments of methods, systems, and non-transitory computer-readable medium having stored computer programs of the present disclosure have been described in considerable detail with specific reference to these illustrated embodiments. It will be apparent, however, that various modifications and changes can be made within the spirit and scope of the embodiments of methods, systems, and non-transitory computer-readable medium having stored computer programs of the present disclosure as described in the foregoing specification, and such modifications and changes are to be considered equivalents and part of this disclosure.

That claimed is:

1. A method for characterizing multiphase fluid flow (MPF) to enhance measuring and monitoring of a flow regime in a segment of pipe for hydrocarbon-production operations, the method comprising the steps of:

sensing an acoustic emission from a MPF, the segment of pipe operable to support the MPF in hydrocarbon-production operations including at least two physical phases;

converting the acoustic emission to an electrical signal;

segmenting the electrical signal into short term, medium term, and long term time series;

assigning positive real numbers to the time series, the positive real numbers including larger values and smaller values, the larger values corresponding to process randomness, and the smaller values corresponding to instances of recognizable patterns in the electrical signal;

categorizing certain positive real numbers as outlier values;

calculating short term, medium term, and long term approximate entropy values for the MPF responsive to the short term, medium term, and long term time series from the electrical signal by performing the following steps:

assigning each of the short term, medium term, and long term time series of data to variables each representing raw data values measured at equally spaced time intervals, forming a sequence of vectors using the variables each representing raw data values, using the sequence of vectors to construct scalar components representing the distance between each respective vector sequence given by the maximum difference in their respective scalar components, calculating each of the short term, medium term, and long term time series approximate entropy values using the scalar components, comparing the short term, medium term, and long term approximate entropy values for the MPF to pre-determined short term, medium term, and long term approximate entropy values; and determining characteristics of the MPF responsive to similarities between the short term, medium term, and long term approximate entropy values for the MPF and the pre-determined short term, medium term, and long term approximate entropy values.

2. The method of claim 1, further comprising the step of displaying the characteristics of the MPF on a user interface, where the user interface is operable to graphically represent at least one flow regime.

3. The method of claim 1, further comprising the step of preamplifying the electrical signal before the step of segmenting the electrical signal.

4. The method of claim 3 further comprising the step of filtering the electrical signal, before segmenting the electrical signal, responsive to programmed cutoff frequencies in a band-pass signal filter derived from an operating frequency and bandwidth of an acoustic emission sensor.

5. The method of claim 4 further comprising the step of converting the electrical signal to a digital signal, before segmenting the electrical signal.

6. The method of claim 1, where the step of sensing an acoustic emission comprises the step of sensing a first acoustic emission, and further comprises the step of sensing a second acoustic emission from the MPF, the second acoustic emission being sensed simultaneously with and at a distance D from the first acoustic emission.

7. The method of claim 6, further comprising the step of calculating an accurate measurement of flow velocity of the MPF in response to the distance D and sensing the first acoustic emission and sensing the second acoustic emission.

8. The method of claim 1, further comprising the step of conducting a principal component analysis, where the principal component analysis comprises the steps of:
gathering acoustic emission data under a variety of flow parameters in situations in which an appropriate Reynolds number is known for the MPF for which data is being gathered;
forming time series of acoustic waveforms;
performing a Fourier Transformation on the data, the data being converted into measurements of acoustic power as a function of frequency;
executing a suite of measurements using a test matrix including different conditions of the MPF including at least one variable selected from the group consisting of: stepped values of watercut, stepped values of total liquid flow, and multiphase flow patterns; and
post-processing the data by applying principal component analysis to the data to determine measurable frequencies relevant to determining the characteristics of the MPF.

9. The method of claim 8 further comprising the step of optimizing the step of sensing an acoustic emission from the MPF to receive the frequencies determined by the principal component analysis to be relevant to determining the characteristics of the MPF.

10. The method of claim 1, further comprising the step of conducting a principal component analysis, where the principal component analysis comprises the steps of:
gathering acoustic emission data under a variety of flow parameters in situations in which an appropriate Reynolds number is known for the MPF for which data is being gathered;
forming time series of acoustic waveforms;
performing a Fourier Transformation on the data, the data being converted into measurements of acoustic power as a function of frequency;
executing a suite of measurements using a test matrix including different conditions of the MPF including at least one variable selected from the group consisting of: stepped values of watercut, stepped values of total liquid flow, and multiphase flow patterns; and
post-processing the data by applying principal component analysis to the data to determine measurable frequencies relevant to determining the characteristics of the MPF.

11. The method of claim 10 further comprising the step of optimizing the step of sensing an acoustic emission from the MPF to receive the frequencies determined by the principal component analysis to be relevant to determining the characteristics of the MPF.

* * * * *